United States Patent
Ummalaneni et al.

(10) Patent No.: US 11,801,105 B2
(45) Date of Patent: *Oct. 31, 2023

(54) SYSTEMS AND METHODS TO CORRECT FOR UNCOMMANDED INSTRUMENT ROLL

(71) Applicant: Auris Health, Inc., Redwood City, CA (US)

(72) Inventors: Ritwik Ummalaneni, San Mateo, CA (US); Allen Jiang, Fremont, CA (US)

(73) Assignee: Auris Health, Inc., Redwood City, CA (US)

(*) Notice: Subject to any disclaimer, the term of this patent is extended or adjusted under 35 U.S.C. 154(b) by 32 days.

This patent is subject to a terminal disclaimer.

(21) Appl. No.: 17/152,085

(22) Filed: Jan. 19, 2021

(65) Prior Publication Data
US 2021/0137621 A1 May 13, 2021

Related U.S. Application Data

(63) Continuation of application No. 16/210,971, filed on Dec. 5, 2018, now Pat. No. 10,987,179.
(Continued)

(51) Int. Cl.
*A61B 34/37* (2016.01)
*A61B 90/00* (2016.01)
(Continued)

(52) U.S. Cl.
CPC .............. *A61B 34/37* (2016.02); *A61B 90/37* (2016.02); *G06T 7/73* (2017.01);
(Continued)

(58) Field of Classification Search
CPC ......... A61B 34/37; A61B 34/20; A61B 90/37; A61B 2034/2051; A61B 2034/2065
See application file for complete search history.

(56) References Cited

U.S. PATENT DOCUMENTS

| 4,644,237 A | 2/1987 | Frushour et al. |
| 4,745,908 A | 5/1988 | Wardle |

(Continued)

FOREIGN PATENT DOCUMENTS

| CN | 1511249 A | 7/2004 |
| CN | 1846181 A | 10/2006 |

(Continued)

OTHER PUBLICATIONS

Blankenstein, Jun. 2008, Dynamic Registration and High Speed Visual Servoing in Robot-Assisted Surgery, Katholieke Universiteit Leuven, Leuven, Belgium, 96 pages.
(Continued)

*Primary Examiner* — Jason M Ip
(74) *Attorney, Agent, or Firm* — Chang & Hale LLP

(57) ABSTRACT

Certain aspects relate to systems, methods, and techniques for correcting for uncommanded instrument roll. A method for adjusting a controller-feedback system in a medical instrument may comprise receiving data from a sensor at or near a distal end of the instrument, determining a tip frame of reference based on the data from the sensor, the tip frame of reference representing a current orientation of the distal end of the instrument, obtaining a desired frame of reference, determining an adjustment to a visual frame of reference or a control frame of reference based on the tip frame of reference and the desired frame of reference, and transforming the visual frame of reference or the control frame of reference.

20 Claims, 27 Drawing Sheets

Related U.S. Application Data

(60) Provisional application No. 62/595,455, filed on Dec. 6, 2017.

(51) Int. Cl.
 *A61B 34/20* (2016.01)
 *G06T 7/73* (2017.01)

(52) U.S. Cl.
 CPC ............... *A61B 2034/2048* (2016.02); *A61B 2034/2051* (2016.02); *A61B 2034/2065* (2016.02); *G06T 2207/30004* (2013.01); *G06T 2207/30196* (2013.01)

(56) References Cited

U.S. PATENT DOCUMENTS

| | | |
|---|---|---|
| 4,748,969 A | 6/1988 | Wardle |
| 5,194,791 A | 3/1993 | Cull |
| 5,251,611 A | 10/1993 | Zehel et al. |
| 5,280,781 A | 1/1994 | Oku |
| 5,408,263 A | 4/1995 | Kikuchi et al. |
| 5,672,877 A | 9/1997 | Liebig et al. |
| 5,769,086 A | 6/1998 | Ritchart et al. |
| 5,899,851 A | 5/1999 | Koninckx |
| 6,004,016 A | 12/1999 | Spector |
| 6,198,974 B1 | 3/2001 | Webster, Jr. |
| 6,246,200 B1 | 6/2001 | Blumenkranz et al. |
| 6,459,926 B1 | 10/2002 | Nowlin et al. |
| 6,690,963 B2 | 2/2004 | Ben-Haim et al. |
| 6,837,846 B2 | 1/2005 | Jaffe et al. |
| 7,197,354 B2 | 3/2007 | Sobe |
| 7,607,440 B2 | 10/2009 | Coste-Maniere et al. |
| 7,763,015 B2 | 7/2010 | Cooper et al. |
| 7,772,541 B2 | 8/2010 | Froggatt et al. |
| 7,963,288 B2 | 6/2011 | Rosenberg et al. |
| 8,335,557 B2 | 12/2012 | Maschke |
| 8,348,931 B2 | 1/2013 | Cooper et al. |
| 8,376,934 B2 | 2/2013 | Takahashi et al. |
| 8,396,595 B2 | 3/2013 | Dariush |
| 8,442,618 B2 | 5/2013 | Strommer et al. |
| 8,469,945 B2 | 6/2013 | Schena |
| 8,498,691 B2 | 7/2013 | Moll et al. |
| 8,506,555 B2 | 8/2013 | Morales |
| 8,554,368 B2 | 10/2013 | Fielding et al. |
| 8,720,448 B2 | 5/2014 | Reis et al. |
| 8,738,181 B2 | 5/2014 | Greer et al. |
| 8,827,948 B2 | 9/2014 | Romo et al. |
| 8,894,610 B2 | 11/2014 | Macnamara et al. |
| 8,929,631 B2 | 1/2015 | Pfister et al. |
| 8,945,095 B2 | 2/2015 | Blumenkranz et al. |
| 9,014,851 B2 | 4/2015 | Wong et al. |
| 9,023,060 B2 | 5/2015 | Cooper et al. |
| 9,129,417 B2 | 9/2015 | Zheng et al. |
| 9,173,713 B2 | 11/2015 | Hart et al. |
| 9,199,372 B2 | 12/2015 | Henderson et al. |
| 9,226,796 B2 | 1/2016 | Bowling et al. |
| 9,256,940 B2 | 2/2016 | Carelsen et al. |
| 9,289,578 B2 | 3/2016 | Walker et al. |
| 9,302,702 B1 | 4/2016 | Schepmann et al. |
| 9,314,306 B2 | 4/2016 | Yu |
| 9,345,456 B2 | 5/2016 | Tsonton et al. |
| 9,358,682 B2 | 6/2016 | Morales |
| 9,452,276 B2 | 9/2016 | Duindam et al. |
| 9,504,604 B2 | 11/2016 | Alvarez |
| 9,522,034 B2 | 12/2016 | Johnson et al. |
| 9,561,083 B2 | 2/2017 | Yu et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,675,422 B2 | 6/2017 | Hourtash et al. |
| 9,713,509 B2 | 7/2017 | Schuh et al. |
| 9,717,563 B2 | 8/2017 | Tognaccini et al. |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,789,608 B2 | 10/2017 | Itkowitz et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,213,264 B2 | 2/2019 | Tanner et al. |
| 10,434,660 B2 | 10/2019 | Meyer et al. |
| 10,454,347 B2 | 10/2019 | Covington et al. |
| 10,464,209 B2 | 11/2019 | Ho et al. |
| 10,470,830 B2 | 11/2019 | Hill et al. |
| 10,482,599 B2 | 11/2019 | Mintz et al. |
| 10,517,692 B2 | 12/2019 | Eyre et al. |
| 10,524,866 B2 | 1/2020 | Srinivasan et al. |
| 10,639,114 B2 | 5/2020 | Schuh et al. |
| 10,667,875 B2 | 6/2020 | DeFonzo et al. |
| 2001/0000040 A1 | 3/2001 | Adams et al. |
| 2001/0021843 A1 | 9/2001 | Bosselmann et al. |
| 2002/0035330 A1 | 3/2002 | Cline et al. |
| 2002/0077533 A1 | 6/2002 | Bieger et al. |
| 2002/0161280 A1 | 10/2002 | Chatenever et al. |
| 2002/0173878 A1 | 11/2002 | Watanabe et al. |
| 2003/0045778 A1 | 3/2003 | Ohline et al. |
| 2003/0181809 A1 | 9/2003 | Hall et al. |
| 2003/0182091 A1 | 9/2003 | Kukuk |
| 2004/0072066 A1 | 4/2004 | Cho et al. |
| 2004/0257021 A1 | 12/2004 | Chang et al. |
| 2005/0043718 A1 | 2/2005 | Madhani et al. |
| 2005/0065400 A1 | 3/2005 | Banik et al. |
| 2005/0107917 A1 | 5/2005 | Smith et al. |
| 2005/0222554 A1 | 10/2005 | Wallace et al. |
| 2005/0234293 A1 | 10/2005 | Yamamoto et al. |
| 2005/0256398 A1 | 11/2005 | Hastings et al. |
| 2005/0261551 A1 | 11/2005 | Couvillon, Jr. et al. |
| 2005/0272975 A1 | 12/2005 | McWeeney et al. |
| 2006/0015096 A1 | 1/2006 | Hauck et al. |
| 2006/0041293 A1 | 2/2006 | Mehdizadeh et al. |
| 2006/0079745 A1 | 4/2006 | Viswanathan |
| 2006/0200026 A1 | 9/2006 | Wallace et al. |
| 2006/0200049 A1 | 9/2006 | Leo et al. |
| 2006/0258938 A1 | 11/2006 | Hoffman et al. |
| 2006/0276775 A1 | 12/2006 | Rosenberg et al. |
| 2007/0013336 A1 | 1/2007 | Nowlin et al. |
| 2007/0043455 A1 | 2/2007 | Viswanathan et al. |
| 2007/0135886 A1 | 6/2007 | Maschke |
| 2007/0142971 A1 | 6/2007 | Schena et al. |
| 2007/0150155 A1 | 6/2007 | Kawai et al. |
| 2007/0156123 A1 | 7/2007 | Moll et al. |
| 2007/0249911 A1 | 10/2007 | Simon |
| 2007/0253599 A1 | 11/2007 | White et al. |
| 2007/0287992 A1 | 12/2007 | Diolaiti et al. |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0108870 A1 | 5/2008 | Wiita et al. |
| 2008/0123921 A1 | 5/2008 | Gielen et al. |
| 2008/0140087 A1 | 6/2008 | Barbagli |
| 2008/0147089 A1 | 6/2008 | Loh et al. |
| 2008/0159653 A1 | 7/2008 | Dunki-Jacobs et al. |

(56) References Cited

U.S. PATENT DOCUMENTS

| | | |
|---|---|---|
| 2008/0231221 A1 | 9/2008 | Ogawa |
| 2008/0249640 A1 | 10/2008 | Vittor et al. |
| 2008/0255505 A1 | 10/2008 | Carlson et al. |
| 2008/0312771 A1 | 12/2008 | Sugiura |
| 2009/0005768 A1 | 1/2009 | Sharareh et al. |
| 2009/0062813 A1 | 3/2009 | Prisco et al. |
| 2009/0076534 A1 | 3/2009 | Shelton et al. |
| 2009/0184825 A1 | 7/2009 | Anderson |
| 2009/0198298 A1 | 8/2009 | Kaiser et al. |
| 2009/0245600 A1 | 10/2009 | Hoffman et al. |
| 2009/0256905 A1 | 10/2009 | Tashiro |
| 2009/0287354 A1 | 11/2009 | Choi |
| 2009/0324161 A1 | 12/2009 | Prisco |
| 2010/0030061 A1 | 2/2010 | Canfield et al. |
| 2010/0030115 A1 | 2/2010 | Fujimoto et al. |
| 2010/0069920 A1 | 3/2010 | Naylor et al. |
| 2010/0076263 A1 | 3/2010 | Tanaka et al. |
| 2010/0121138 A1 | 5/2010 | Goldenberg et al. |
| 2010/0168918 A1 | 7/2010 | Zhao et al. |
| 2010/0204713 A1 | 8/2010 | Morales |
| 2010/0228266 A1 | 9/2010 | Hourtash |
| 2010/0234856 A1 | 9/2010 | Stoianovici et al. |
| 2010/0256812 A1 | 10/2010 | Tsusaka et al. |
| 2011/0009880 A1 | 1/2011 | Prisco et al. |
| 2011/0021926 A1 | 1/2011 | Spencer et al. |
| 2011/0082366 A1 | 4/2011 | Scully et al. |
| 2011/0082462 A1 | 4/2011 | Suarez et al. |
| 2011/0137122 A1 | 6/2011 | Kawai |
| 2011/0153252 A1 | 6/2011 | Govari et al. |
| 2011/0160570 A1 | 6/2011 | Kariv et al. |
| 2011/0196199 A1 | 8/2011 | Donhowe et al. |
| 2011/0218676 A1 | 9/2011 | Okazaki |
| 2011/0257480 A1 | 10/2011 | Takahashi et al. |
| 2011/0258842 A1 | 10/2011 | Dukesherer et al. |
| 2011/0276058 A1 | 11/2011 | Choi et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0069167 A1 | 3/2012 | Liu et al. |
| 2012/0071752 A1 | 3/2012 | Sewell et al. |
| 2012/0071822 A1 | 3/2012 | Romo et al. |
| 2012/0071894 A1 | 3/2012 | Tanner et al. |
| 2012/0123441 A1 | 5/2012 | Au et al. |
| 2012/0130217 A1 | 5/2012 | Kauphusman et al. |
| 2012/0209293 A1 | 8/2012 | Carlson et al. |
| 2012/0215094 A1 | 8/2012 | Rahimian et al. |
| 2012/0253276 A1 | 10/2012 | Govari et al. |
| 2012/0283745 A1 | 11/2012 | Goldberg et al. |
| 2012/0289777 A1 | 11/2012 | Chopra et al. |
| 2012/0302869 A1 | 11/2012 | Koyrakh et al. |
| 2012/0328077 A1 | 12/2012 | Bouvier |
| 2013/0018306 A1 | 1/2013 | Ludwin |
| 2013/0083310 A1 | 4/2013 | Ramamurthy et al. |
| 2013/0085330 A1 | 4/2013 | Ramamurthy et al. |
| 2013/0090530 A1 | 4/2013 | Ramamurthy et al. |
| 2013/0102846 A1 | 4/2013 | Sjostrom et al. |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle et al. |
| 2013/0204124 A1 | 8/2013 | Duindam et al. |
| 2013/0218005 A1 | 8/2013 | Desai et al. |
| 2013/0303891 A1 | 11/2013 | Chopra et al. |
| 2013/0303892 A1 | 11/2013 | Zhao et al. |
| 2013/0325030 A1 | 12/2013 | Hourtash et al. |
| 2014/0114180 A1 | 4/2014 | Jain et al. |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222207 A1 | 8/2014 | Bowling et al. |
| 2014/0235943 A1 | 8/2014 | Paris et al. |
| 2014/0277333 A1 | 9/2014 | Lewis et al. |
| 2014/0296870 A1 | 10/2014 | Stern et al. |
| 2014/0309649 A1 | 10/2014 | Alvarez et al. |
| 2014/0316420 A1 | 10/2014 | Ballard et al. |
| 2014/0343416 A1 | 11/2014 | Panescu et al. |
| 2014/0343569 A1 | 11/2014 | Turner |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0073267 A1 | 3/2015 | Brannan et al. |
| 2015/0088161 A1 | 3/2015 | Hata et al. |
| 2015/0104284 A1 | 4/2015 | Riedel et al. |
| 2015/0119628 A1 | 4/2015 | Bharat et al. |
| 2015/0119638 A1 | 4/2015 | Yu et al. |
| 2015/0150635 A1 | 6/2015 | Kilroy et al. |
| 2015/0164594 A1 | 6/2015 | Romo et al. |
| 2015/0164596 A1 | 6/2015 | Romo et al. |
| 2015/0202015 A1 | 7/2015 | Elhawary et al. |
| 2015/0223902 A1 | 8/2015 | Walker et al. |
| 2015/0255782 A1 | 9/2015 | Kim et al. |
| 2015/0265359 A1 | 9/2015 | Camarillo |
| 2015/0265368 A1 | 9/2015 | Chopra et al. |
| 2015/0265807 A1 | 9/2015 | Park et al. |
| 2015/0272427 A1 | 10/2015 | Haque et al. |
| 2015/0305650 A1 | 10/2015 | Hunter et al. |
| 2015/0311838 A1 | 10/2015 | Moule et al. |
| 2015/0335480 A1 | 11/2015 | Alvarez et al. |
| 2015/0342695 A1 | 12/2015 | He et al. |
| 2015/0359597 A1 | 12/2015 | Gombert et al. |
| 2015/0374956 A1 | 12/2015 | Bogusky et al. |
| 2016/0000414 A1 | 1/2016 | Brown et al. |
| 2016/0000495 A1 | 1/2016 | Elliott et al. |
| 2016/0001038 A1 | 1/2016 | Romo et al. |
| 2016/0005168 A1 | 1/2016 | Merlet et al. |
| 2016/0005220 A1 | 1/2016 | Weingarten et al. |
| 2016/0005576 A1 | 1/2016 | Tsukamoto et al. |
| 2016/0016319 A1 | 1/2016 | Remirez et al. |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper et al. |
| 2016/0075030 A1 | 3/2016 | Takahashi et al. |
| 2016/0081568 A1 | 3/2016 | Kolberg et al. |
| 2016/0100772 A1 | 4/2016 | Ikuma et al. |
| 2016/0128781 A1 | 5/2016 | Blohm et al. |
| 2016/0128992 A1 | 5/2016 | Hudson et al. |
| 2016/0183841 A1 | 6/2016 | Duindam et al. |
| 2016/0206389 A1 | 7/2016 | Miller et al. |
| 2016/0228032 A1 | 8/2016 | Walker et al. |
| 2016/0270865 A1 | 9/2016 | Landey et al. |
| 2016/0278865 A1 | 9/2016 | Capote et al. |
| 2016/0287053 A1 | 10/2016 | Miura et al. |
| 2016/0287111 A1 | 10/2016 | Jacobsen et al. |
| 2016/0287279 A1 | 10/2016 | Bovay et al. |
| 2016/0287346 A1 | 10/2016 | Hyodo et al. |
| 2016/0331469 A1 | 11/2016 | Hall et al. |
| 2016/0338787 A1 | 11/2016 | Popovic et al. |
| 2016/0346038 A1 | 12/2016 | Helgeson et al. |
| 2016/0346924 A1 | 12/2016 | Hasegawa et al. |
| 2016/0354057 A1 | 12/2016 | Hansen et al. |
| 2016/0360947 A1 | 12/2016 | Iida et al. |
| 2016/0360949 A1 | 12/2016 | Hyodo et al. |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0068796 A1 | 3/2017 | Passerini et al. |
| 2017/0100197 A1 | 4/2017 | Zubiate et al. |
| 2017/0100199 A1 | 4/2017 | Yu et al. |
| 2017/0106904 A1 | 4/2017 | Hanson et al. |
| 2017/0119413 A1 | 5/2017 | Romo |
| 2017/0119481 A1 | 5/2017 | Romo et al. |
| 2017/0135557 A1 | 5/2017 | Inoue |
| 2017/0151027 A1 | 6/2017 | Walker et al. |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0189118 A1 | 7/2017 | Chopra et al. |
| 2017/0202627 A1 | 7/2017 | Sramek et al. |
| 2017/0209073 A1 | 7/2017 | Sramek et al. |
| 2017/0245854 A1 | 8/2017 | Zemlok et al. |
| 2017/0245885 A1 | 8/2017 | Lenker et al. |

(56) References Cited

U.S. PATENT DOCUMENTS

| | | |
|---|---|---|
| 2017/0251988 A1 | 9/2017 | Weber et al. |
| 2017/0280978 A1 | 10/2017 | Yamamoto et al. |
| 2017/0281049 A1 | 10/2017 | Yamamoto et al. |
| 2017/0290631 A1 | 10/2017 | Lee et al. |
| 2017/0303889 A1 | 10/2017 | Grim et al. |
| 2017/0304015 A1 | 10/2017 | Tavallaei et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0064498 A1 | 3/2018 | Kapadia et al. |
| 2018/0177383 A1 | 6/2018 | Noonan et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi et al. |
| 2018/0271604 A1 | 9/2018 | Grout et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 5/2019 | Alvarez et al. |
| 2019/0167367 A1 | 6/2019 | Walker et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0209252 A1 | 7/2019 | Walker et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000533 A1 | 1/2020 | Schuh et al. |
| 2020/0008874 A1 | 1/2020 | Barbagli et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054408 A1 | 2/2020 | Schuh et al. |
| 2020/0060516 A1 | 2/2020 | Baez, Jr. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0188043 A1 | 6/2020 | Yu et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |

FOREIGN PATENT DOCUMENTS

| | | |
|---|---|---|
| CN | 1857877 A | 11/2006 |
| CN | 101325920 A | 12/2008 |
| CN | 102316817 A | 1/2012 |
| CN | 102458295 A | 5/2012 |
| CN | 102711586 A | 10/2012 |
| CN | 102973317 A | 3/2013 |
| CN | 103565529 A | 2/2014 |
| CN | 103735313 A | 4/2014 |
| CN | 103767659 A | 5/2014 |
| CN | 103930063 A | 7/2014 |
| CN | 104684502 A | 6/2015 |
| CN | 105030331 A | 11/2015 |
| CN | 105511881 A | 4/2016 |
| CN | 105559850 A | 5/2016 |
| CN | 107028659 A | 8/2017 |
| CN | 104931059 B | 9/2018 |
| CN | 105559886 B | 6/2019 |
| DE | 102013100605 A1 | 7/2014 |
| EP | 1250986 A2 | 10/2002 |
| EP | 1566150 A2 | 8/2005 |
| EP | 1800593 A1 | 6/2007 |
| EP | 1800593 A1 | 6/2007 |
| EP | 2158834 A1 | 3/2010 |
| EP | 2392435 A2 | 12/2011 |
| EP | 2923669 A1 | 9/2015 |
| EP | 3025630 A1 | 6/2016 |
| JP | 2000079087 A | 3/2000 |
| JP | 2003265500 A | 9/2003 |
| JP | 107328016 B | 7/2004 |
| JP | 2006116289 A | 5/2006 |
| JP | 2006218027 | 3/2008 |
| JP | 2008528130 A | 7/2008 |
| JP | 2009509654 A | 3/2009 |
| JP | 2009524530 A | 7/2009 |
| JP | 2011088260 A | 5/2011 |
| JP | 2013510662 A | 3/2013 |
| JP | 2014023818 A | 2/2014 |
| JP | 2014083156 A | 5/2014 |
| RU | 2569699 C2 | 11/2015 |
| WO | 0156457 A1 | 8/2001 |
| WO | 2004029782 A2 | 4/2004 |
| WO | 2005078128 A1 | 8/2005 |
| WO | 2006035693 A1 | 4/2006 |
| WO | 2006122061 A1 | 11/2006 |
| WO | 2009120940 A2 | 10/2009 |
| WO | 2011132409 A1 | 10/2011 |
| WO | 2012044334 A2 | 4/2012 |
| WO | 2014114551 A1 | 7/2014 |
| WO | 2015142957 A1 | 9/2015 |
| WO | 2017048194 A1 | 3/2017 |

OTHER PUBLICATIONS

EP Examination Report for appl No. 18886855.8, dated Dec. 23, 2021, 6 pages.

(56) References Cited

OTHER PUBLICATIONS

International Search Report dated Mar. 6, 2019 in Application No. PCT/US18/064126, 2 pages.
International Written Opinion dated Mar. 6, 2019 in Application No. PCT/US18/064126, 5 pages.
Kukuk, Oct. 5, 2001, TBNA-protocols: Guiding TransBronchial Needle Aspirations Without a Computer in the Operating Room, MICCAI 2001, 2208:997-1006.
Lawton et al., 1999, Ribbons and groups: A thin rod theory for catheters and filaments, J. Phys. A., 1999, 32:1709-1735.
Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12, 1 page.
EP Search Report for appl No. 18886855, dated May 11, 2021, 2 pages.
EP Search report opinion for appl No. 18886855.8, dated May 11, 2021, 7 pages.
Non-Final Rejection for U.S. Appl. No. 16/210,971, dated Aug. 2, 2019, 11 pages.
Non-Final Rejection for U.S. Appl. No. 16/210,971, dated Feb. 5, 2020, 22 pages.
Notice of Allowance for U.S. Appl. No. 16/210,971, dated Oct. 9, 2020, 13 pages.
EP Examination Report for Appl. No. 18886855.8, dated Jan. 23, 2023, 4 pages.
JP Office Action for Appl. No. 2020-530977, dated Feb. 22, 2023, 11 pages.
KR Preliminary Rejection for Appl. No. 10-2020-7014158, dated Aug. 4, 2023, 8 pages.

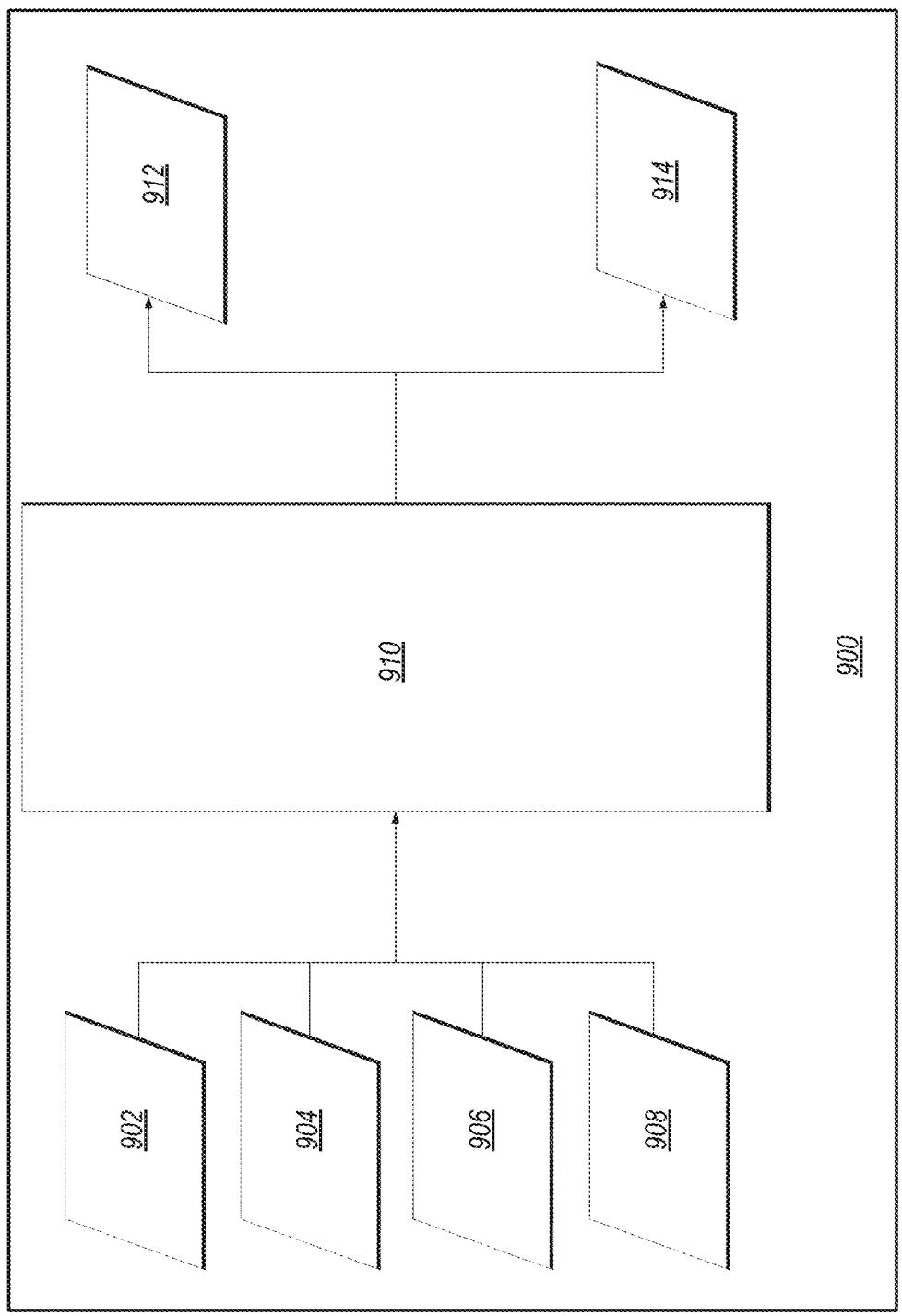

SYSTEMS AND METHODS TO CORRECT FOR UNCOMMANDED INSTRUMENT ROLL

INCORPORATION BY REFERENCE TO ANY PRIORITY APPLICATIONS

This application is a continuation of U.S. application Ser. No. 16/210,971, filed Dec. 5, 2018, which claims priority to U.S. Provisional Application No. 62/595,455, filed Dec. 6, 2017, the entirety of each which is incorporated herein by reference. Any and all applications for which a foreign or domestic priority claim is identified in the Application Data Sheet as filed with the present application are hereby incorporated by reference under 37 CFR 1.57.

TECHNICAL FIELD

The systems and methods disclosed herein are directed to medical procedures, and more particularly to systems and methods for correcting for uncommanded instrument roll.

BACKGROUND

Medical procedures such as endoscopy (e.g., bronchoscopy) may involve accessing and visualizing the inside of a patient's lumen (e.g., airways, bronchi, or bronchioles) for diagnostic and/or therapeutic purposes. During a procedure, a flexible tubular instrument (e.g., an endoscope or a catheter) may be inserted into the patient's body and a tool (e.g., a grasping forcep, a biopsy forcep, a cytology brush, a balloon dilator, a snare, a needle, and/or a basket) can be passed through the flexible tubular instrument to a tissue site identified for diagnosis and/or treatment.

SUMMARY

The systems, methods and devices of this disclosure each have several innovative aspects, no single one of which is solely responsible for the desirable attributes disclosed herein.

In one aspect, there is provided a method for adjusting a controller-feedback system in a robotically controlled medical instrument inserted into a patient, comprising: receiving data from at least one imaging device or location sensor at a distal end of the instrument, determining a tip frame of reference based on the data from the at least one imaging device or location sensor, the tip frame of reference representing a current orientation of the distal end of the instrument, obtaining a desired frame of reference representing a frame of reference relative to an anatomy frame of reference or a global frame of reference, determining an adjustment to a visual frame of reference or a control frame of reference based on the tip frame of reference and the desired frame of reference, and transforming the visual frame of reference or the control frame of reference based on the determined adjustment.

The method may also include one or more of the following features in any combination: (a) wherein the at least one location sensor comprises an electromagnetic (EM) sensor; (b) wherein the visual frame of reference represents an image from the imaging device at the distal end of the instrument; (c) wherein the control frame of reference represents an orientation of a control system of the instrument; (d) wherein obtaining the desired frame of reference is based on one or more anatomical features of the patient; (e) wherein obtaining the desired frame of reference is based on one or more pixel values of an image representing the one or more anatomical features of the patient; (f) wherein obtaining the desired frame of reference is based on one or more anatomical features of a main carina of the patient; (g) wherein obtaining the desired frame of reference is based on data from one or more EM patches positioned on the patient; (h) wherein obtaining the desired frame of reference is based on the tip frame of reference; (i) wherein determining the adjustment is based on comparing between one or more features derived from at least one image of an anatomical feature and one or more features derived from at least one model of the anatomical feature; (j) wherein the at least one image of an anatomical feature is obtained from the imaging device at the distal end of the instrument; (k) wherein determining the adjustment is based on comparing between data from one or more EM sensors in the distal end of the instrument and data from one or more EM patches positioned on the patient; (l) wherein determining the adjustment is based on data from an accelerometer configured to measure a force of gravity; (m) wherein transforming the visual frame of reference or the control frame of reference comprises rotating the visual frame of reference or the control frame of reference with respect to a longitudinal axis of the instrument; (n) wherein transforming the visual frame of reference or the control frame of reference comprises rotating the visual frame of reference or the control frame of reference to align with the tip frame of reference or the desired frame of reference; (o) wherein transforming the visual frame of reference or the control frame of reference is based on a user input; (p) verifying the transformed visual frame of reference or the transformed control frame of reference; and/or (q) wherein verifying the transformed visual frame of reference or the transformed control frame of reference comprises: moving the instrument in one direction, calculating an expected change in the visual frame of reference or the control frame of reference in response to the movement of the instrument, and comparing between an actual change in the visual frame of reference or the control frame of reference and the expected change.

In another aspect, there is provided a system configured to transform a control frame of a medical instrument configured to be inserted into a patient in which the system comprises: a control system configured to determine movement of the medical instrument, at least one computer-readable memory having stored thereon executable instructions; and one or more processors in communication with the at least one computer-readable memory and configured to execute the instructions to cause the system to at least: obtain a control frame of reference representing a relationship between a motor control command and a motor output of the medical instrument, determine a tip frame of reference based on data from at least one imaging device or location sensor at a distal end of the medical instrument, the tip frame of reference representing a current orientation of the distal end of the medical instrument, obtain a desired frame of reference, and transform the control frame of reference based on the tip frame of reference and the desired frame of reference.

The system may also include one or more of the following features in any combination: (a) wherein the at least one location sensor comprises an electromagnetic (EM) sensor; (b) wherein the one or more processors in communication with the at least one computer-readable memory are configured to execute the instructions to cause the system to at least: receive the tip frame of reference from the medical instrument; (c) wherein the one or more processors in communication with the at least one computer-readable memory are configured to execute the instructions to cause the system to at least: receive data from a second sensor at the distal end of the medical instrument and determine the tip frame of reference based on the data from the second sensor; (d) wherein the second sensor at the distal end of the instrument comprises at least one imaging device or location sensor; (e) wherein the second sensor comprises an electromagnetic (EM) sensor; (f) wherein the one or more processors in communication with the at least one computer-readable memory are configured to execute the instructions to cause the system to at least receive the control frame of reference from the control system; (g) wherein the one or more processors in communication with the at least one computer-readable memory are configured to execute the instructions to cause the system to at least move the medical instrument in one direction and determine the control frame of reference based on the movement of the medical instrument; (h) wherein the one or more processors in communication with the at least one computer-readable memory are configured to execute the instructions to cause the system to at least receive a visual frame of reference from the instrument and transform the visual frame of reference based on the tip frame of reference and the desired frame of reference; (i) wherein the one or more processors in communication with the at least one computer-readable memory are configured to execute the instructions to cause the system to at least receive data from the at least one sensor at the distal end of the medical instrument, determine a visual frame of reference based on the data from the at least one sensor, and transform the visual frame of reference based on the tip frame of reference and the desired frame of reference; (j) wherein the one or more processors in communication with the at least one computer-readable memory are configured to execute the instructions to cause the system to at least: determine the desired frame of reference based on one or more anatomical features of the patient; (k) wherein the one or more processors in communication with the at least one computer-readable memory are configured to execute the instructions to cause the system to at least: determine the desired frame of reference based on one or more pixel values of an image representing the one or more anatomical features of the patient; (l) wherein the one or more processors in communication with the at least one computer-readable memory are configured to execute the instructions to cause the system to at least: determine the desired frame of reference based on data from one or more EM patches positioned on the patient; (m) wherein the one or more processors in communication with the at least one computer-readable memory are configured to execute the instructions to cause the system to at least determine one or more differences between at least one image of an anatomical feature and at least one model of the anatomical feature, and transform the control frame of reference based on the differences between the at least one image and the at least one model; (n) wherein the one or more processors in communication with the at least one computer-readable memory are configured to execute the instructions to cause the system to at least rotate the control frame of reference with respect to a longitudinal axis of the medical instrument to align with the desired frame of reference; (o) wherein the one or more processors in communication with the at least one computer-readable memory are configured to execute the instructions to cause the system to at least: transform the control frame of reference based on a user input; (p) wherein the one or more processors in communication with the at least one computer-readable memory are configured to further execute the instructions to cause the system to at least: verify the transformed control frame of reference; (q) wherein the one or more processors in communication with the at least one computer-readable memory are configured to further execute the instructions to cause the system to at least move the medical instrument in one direction, determine an expected change in the control frame of reference in response to the movement of the medical instrument, and compare between an actual change in the control frame of reference and the expected change; and/or (r) wherein the one or more processors in communication with the at least one computer-readable memory are configured to further execute the instructions to cause the system to at least obtain a sheath frame of reference representing an orientation of a distal end of a sheath configured to slidably cover the medical instrument, and transform the sheath frame of reference based on the control frame of reference or the desired frame of reference.

In yet another aspect, there is provided a robotically controlled steerable instrument system that comprises a steerable instrument comprising a proximal end, a distal end, a channel extending therethrough, and at least one sensor at the distal end, the instrument configured to be inserted into a patient, one or more pullwires extending through and coupled to at least a portion of the steerable instrument, a robotic instrument driver, a control system communicatively coupled to the instrument driver and configured to actuate the one or more pullwires, at least one computer-readable memory having stored thereon executable instructions, and one or more processors in communication with the at least one computer-readable memory and configured to execute the instructions to cause the system to at least obtain a control frame of reference representing relationship between a motor control command and a motor output of the instrument, determine a tip frame of reference based on data from at least one imaging device or location sensor at a distal end of the instrument, the tip frame of reference representing a current orientation of the distal end of the instrument, obtain a desired frame of reference, and transform the control frame of reference based on the tip frame of reference and the desired frame of reference.

The system may also include one or more of the following features in any combination: (a) wherein the location sensor comprises an electromagnetic (EM) sensor; (b) wherein the one or more processors in communication with the at least one computer-readable memory are configured to execute the instructions to cause the system to at least receive data from the at least one sensor and determine the tip frame of reference based on the data from the at least one sensor; (c) wherein the one or more processors in communication with the at least one computer-readable memory are configured to execute the instructions to cause the system to at least: receive the control frame of reference from the control system; (d) wherein the one or more processors in communication with the at least one computer-readable memory are configured to execute the instructions to cause the system to at least actuate the one or more pullwires to move the portion of the instrument and determine the control frame of reference based on the movement of the portion of the instrument; (e) wherein the one or more processors in communication with the at least one computer-readable memory are configured to execute the instructions to cause the system to at least receive data from the at least one sensor, determine a visual frame of reference based on the data from the at least one sensor, and transform the visual frame of reference based on the tip frame of reference and the desired frame of reference; (f) wherein the one or more processors in communication with the at least one computer-readable memory are configured to execute the instructions to cause the system to at least: determine the desired frame of reference based on one or more anatomical features of the patient; (g) wherein the one or more processors in communication with the at least one computer-readable memory are configured to execute the instructions to cause the system to at least determine the desired frame of reference based on data from one or more EM patches positioned on the patient; (h) wherein the one or more processors in communication with the at least one computer-readable memory are configured to execute the instructions to cause the system to at least determine one or more differences between at least one image of an anatomical feature and at least one model of the anatomical feature, and transform the control frame of reference based on the differences between the at least one image and the at least one model; (i) wherein the one or more processors in communication with the at least one computer-readable memory are configured to execute the instructions to cause the system to at least rotate the control frame of reference with respect to a longitudinal axis of the instrument to align with the desired frame of reference; (j) wherein the one or more processors in communication with the at least one computer-readable memory are configured to execute the instructions to cause the system to at least: transform the control frame of reference based on a user input; (k) wherein the one or more processors in communication with the at least one computer-readable memory are configured to further execute the instructions to cause the system to at least verify the transformed control frame of reference; (l) wherein the one or more processors in communication with the at least one computer-readable memory are configured to further execute the instructions to cause the system to at least actuate the one or more pullwires to move the portion of the instrument, determine an expected change in the control frame of reference in response to the movement of the portion of the instrument; and compare between an actual change in the control frame of reference and the expected change; and/or (m) wherein the steerable instrument further comprises a sheath configured to slidably cover at least a portion of the instrument, and wherein the one or more processors in communication with the at least one computer-readable memory are configured to further execute the instructions to cause the system to at least obtain a sheath frame of reference representing an orientation of a distal end of the sheath, and transform the sheath frame of reference based on the control frame of reference or the desired frame of reference.

In one aspect, there is provided a non-transitory computer readable storage medium having stored thereon instructions that, when executed, cause at least one processor to at least: obtain a control frame of reference representing relationship between a motor control command and a motor output of a medical instrument configured to be inserted into a patient; determine a tip frame of reference based on data from at least one imaging device or location sensor at a distal end of the medical instrument, the tip frame of reference representing a current orientation of the distal end of the medical instrument, obtain a desired frame of reference based on data from the at least one imaging device or location sensor positioned on the patient, and determine one or more differences between (1) the control frame of reference and (2) the desired frame of reference.

The non-transitory computer readable storage medium may also comprise one or more of the following features in any combination: (a) wherein the instructions that, when executed, cause at least one processor to at least obtain a control frame of reference representing relationship between a motor control command and a motor output of a medical instrument configured to be inserted into a patient, determine a tip frame of reference based on data from at least one imaging device or location sensor at a distal end of the medical instrument, the tip frame of reference representing a current orientation of the distal end of the medical instrument, obtain a desired frame of reference based on data from the at least one imaging device or location sensor positioned on the patient, and determine one or more differences between the control frame of reference and the desired frame of reference; (b) wherein the at least one location sensor comprises an electromagnetic (EM) sensor; (c) wherein the instructions, when executed, cause the at least one processor to at least: receive a tip frame of reference from the medical instrument; (d) wherein the instructions, when executed, cause the at least one processor to at least determine the desired frame of reference based on the tip frame of reference; (e) wherein the instructions, when executed, cause the at least one processor to at least transform a visual frame of reference or the control frame of reference based on the determined differences; (f) wherein the visual frame of reference represents an orientation of the at least one imaging device at the distal end of the medical instrument; (g) wherein the instructions, when executed, cause the at least one processor to at least determine the desired frame of reference based on one or more anatomical features of the patient; (h) wherein the instructions, when executed, cause the at least one processor to at least: determine the one or more differences by comparing between one or more features derived from at least one image of an anatomical feature and one or more features derived from at least one model of the anatomical feature; (i) wherein the instructions, when executed, cause the at least one processor to at least determine the one or more differences by comparing between data from the at least one location sensor in the distal end of the medical instrument and data from one or more EM patches positioned on the patient; (j) wherein the instructions, when executed, cause the at least one processor to at least: transform the control frame of reference by rotating the control frame of reference with respect to a longitudinal axis of the medical instrument to align with the desired frame of reference; (k) wherein the instructions, when executed, cause the at least one processor to at least transform the control frame of reference based on a user input; (l) wherein the instructions, when executed, cause the at least one processor to at least verify the transformed control frame of reference; and/or (m) wherein the instructions, when executed, cause the at least one processor to at least move the medical instrument in one direction, calculate an expected change in the control frame of reference in response to the movement of the medical instrument, and compare between an actual change in the control frame of reference and the expected change.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 26 describes a control system configured to correct for uncommanded instrument roll.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

As used herein, "distal" refers to the end of a scope, instrument, or tool positioned closest to the patient during use, and "proximal" refers to the end of the scope, instrument, or tool positioned closest to the operator (e.g., a physician or robotic control system). Stated differently, the relative positions of components of the scope, instrument, tool, and/or the robotic system are described herein from the vantage point of the operator.

As used herein, the terms "about" or "approximately" refer to a range of measurements of a length, thickness, a quantity, time period, or other measurable values. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
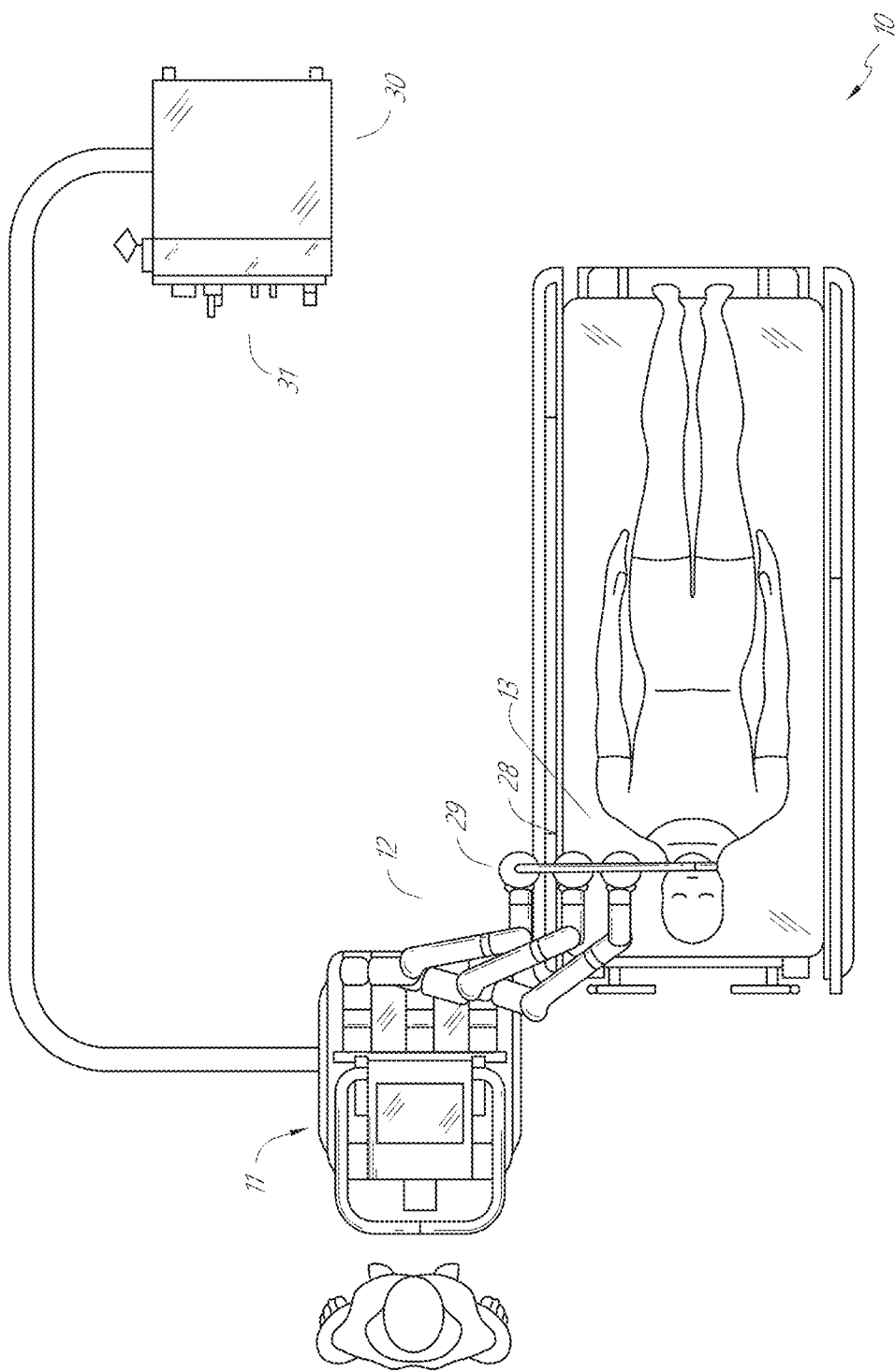
FIG. 1 illustrates an embodiment of a cart-based robotic system arranged for diagnostic and/or therapeutic bronchoscopy procedure(s).
Figure 2:
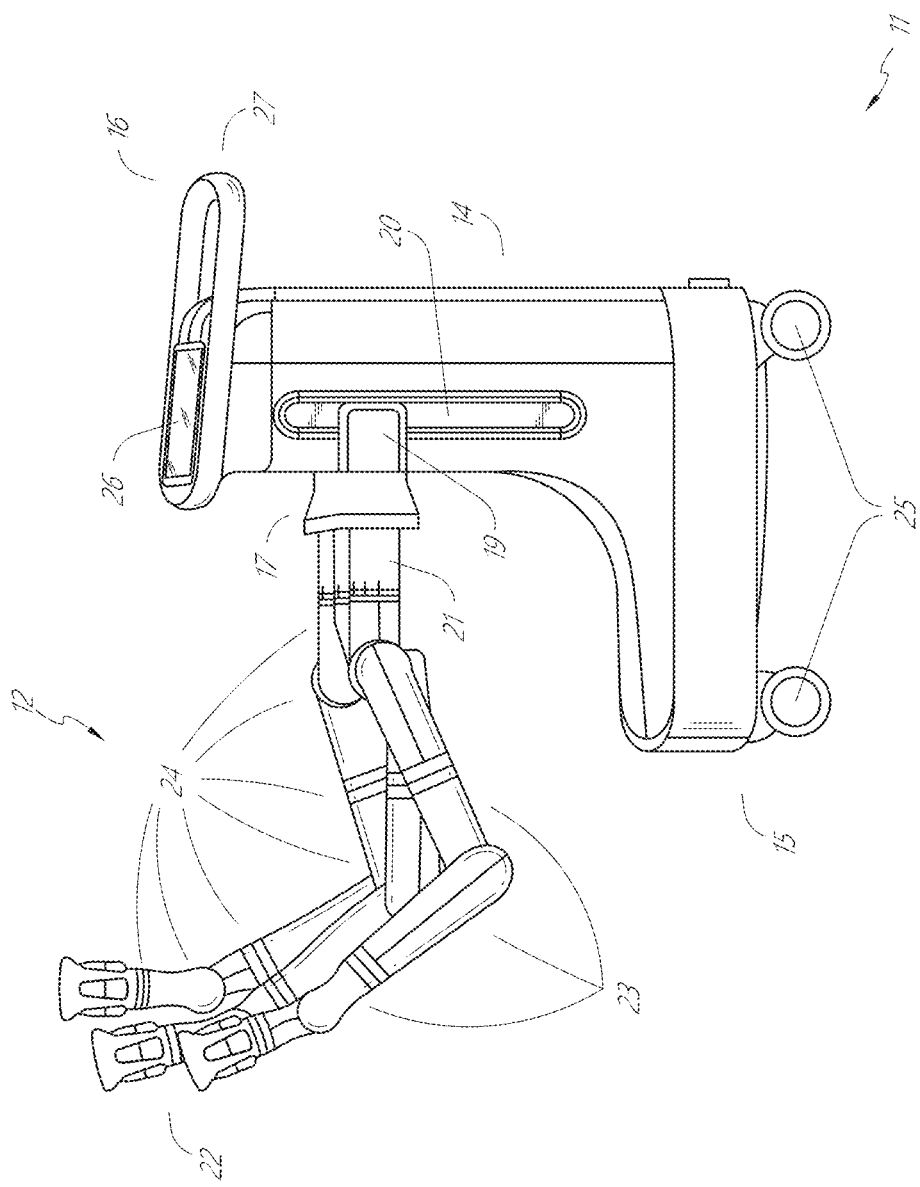
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed EM sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician may view the console 16, robotic arms 12, and patient while operating the console 16 from behind the cart 11. As shown, the console 16 also includes a handle 27 to assist with maneuvering and stabilizing cart 11.

Figure 3:
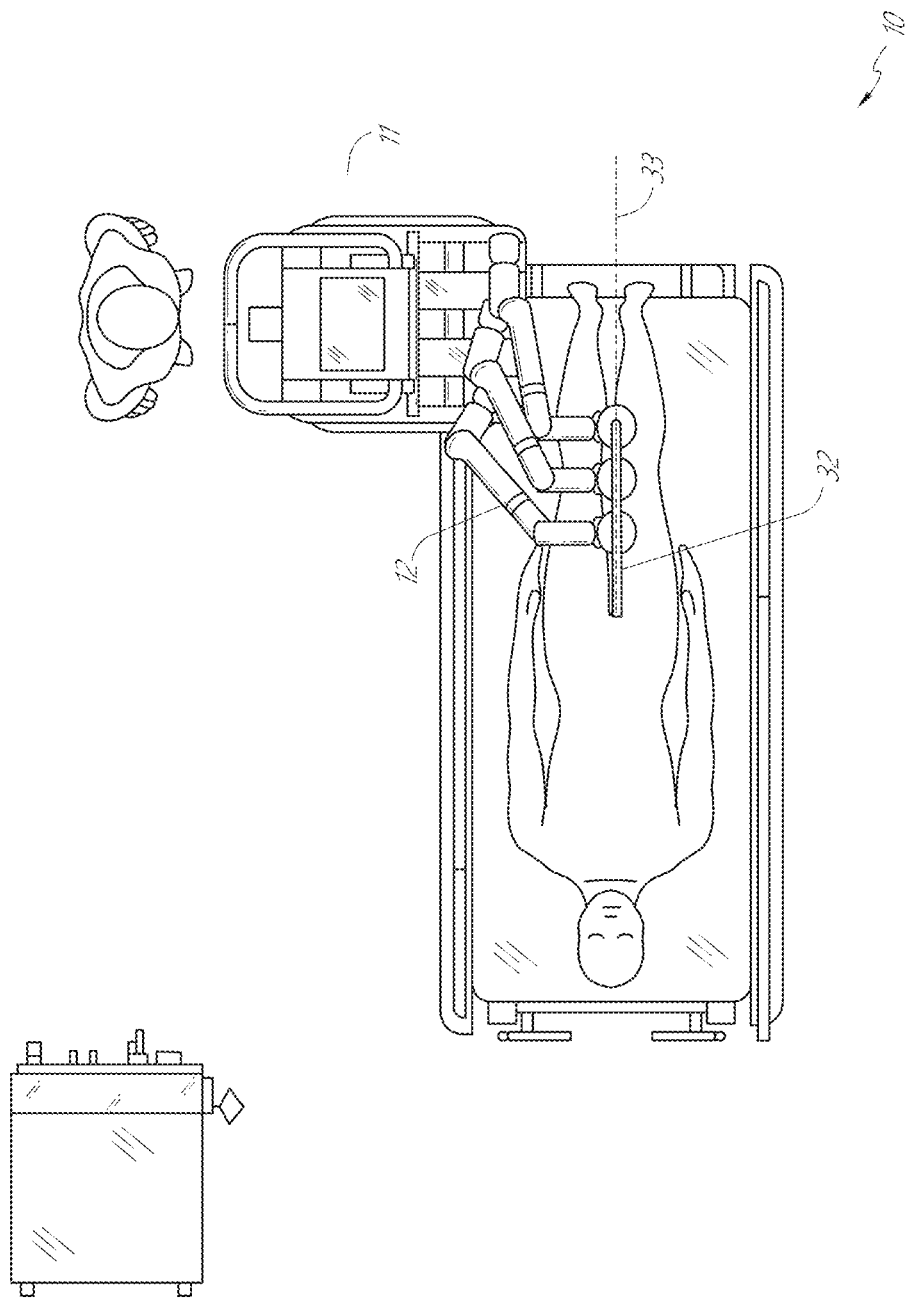
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
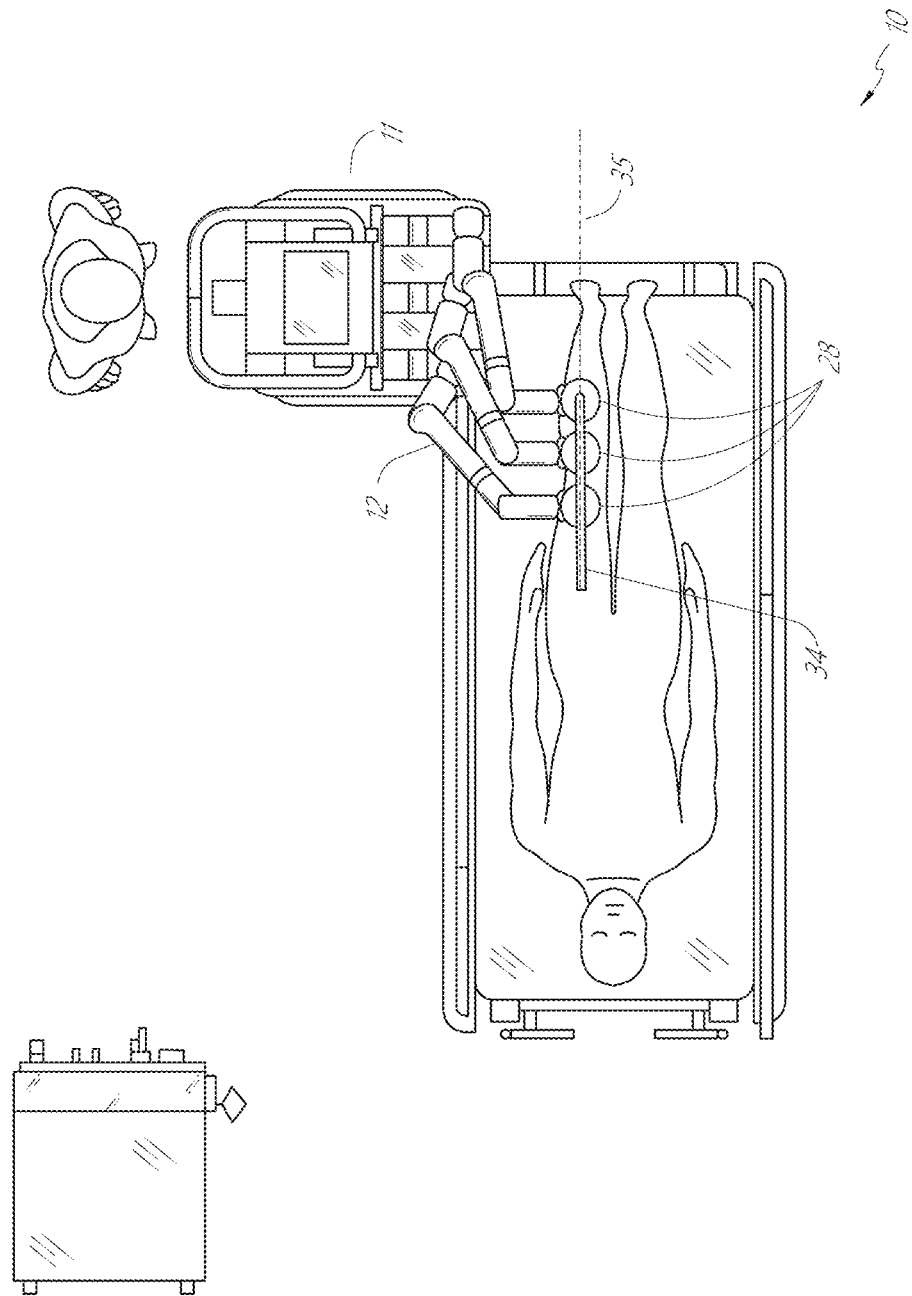
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
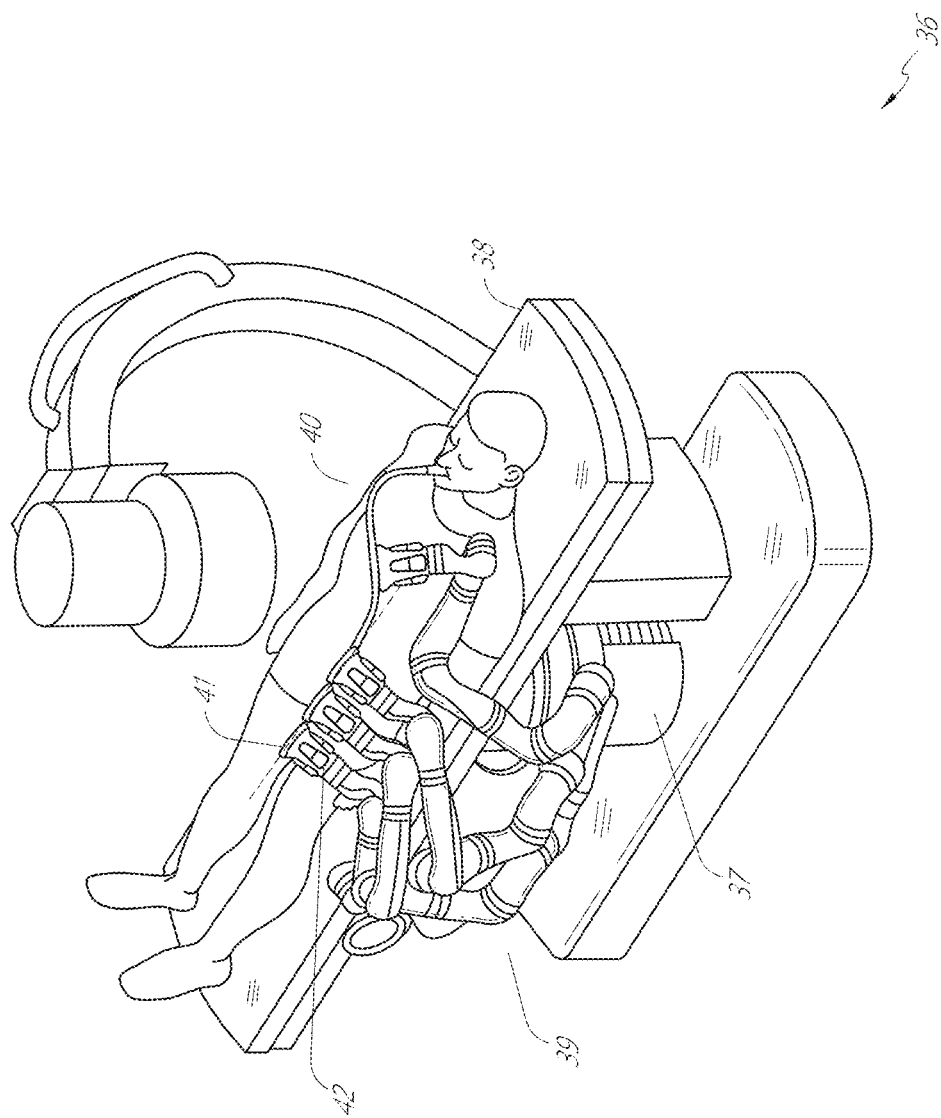
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
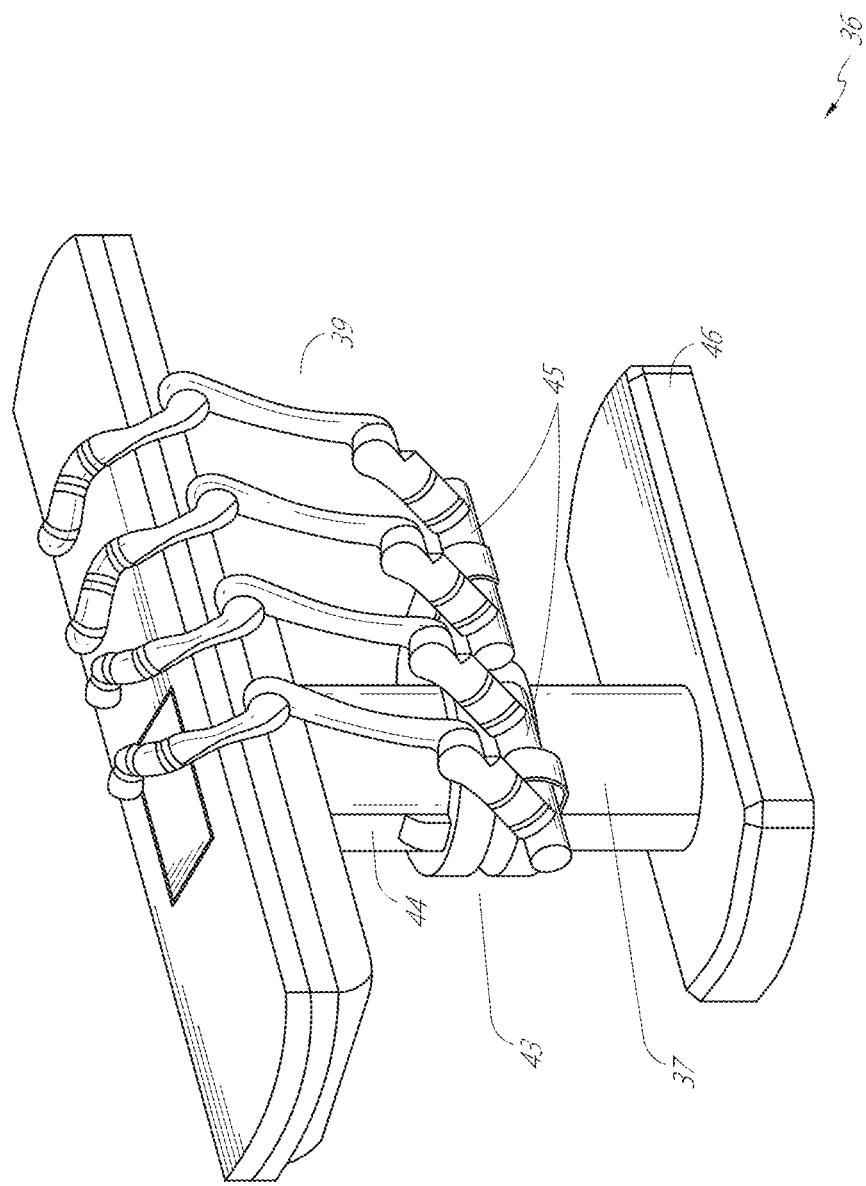
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
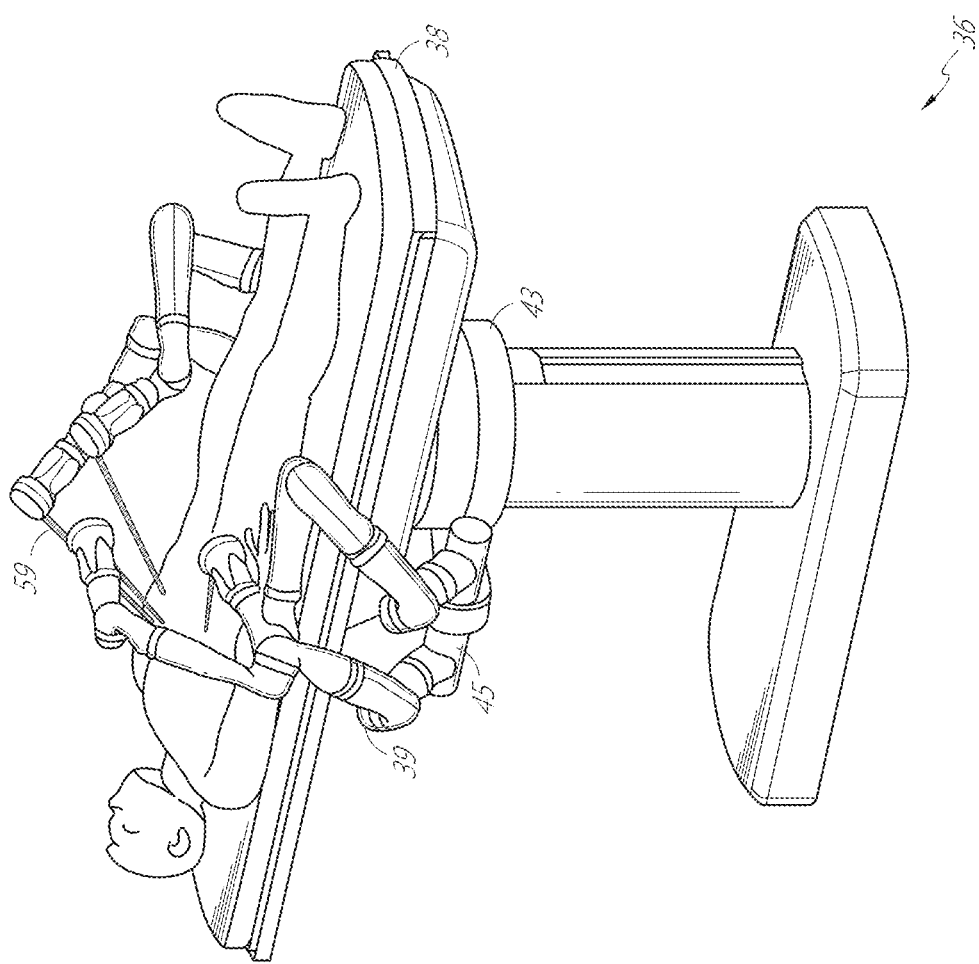
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may be provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
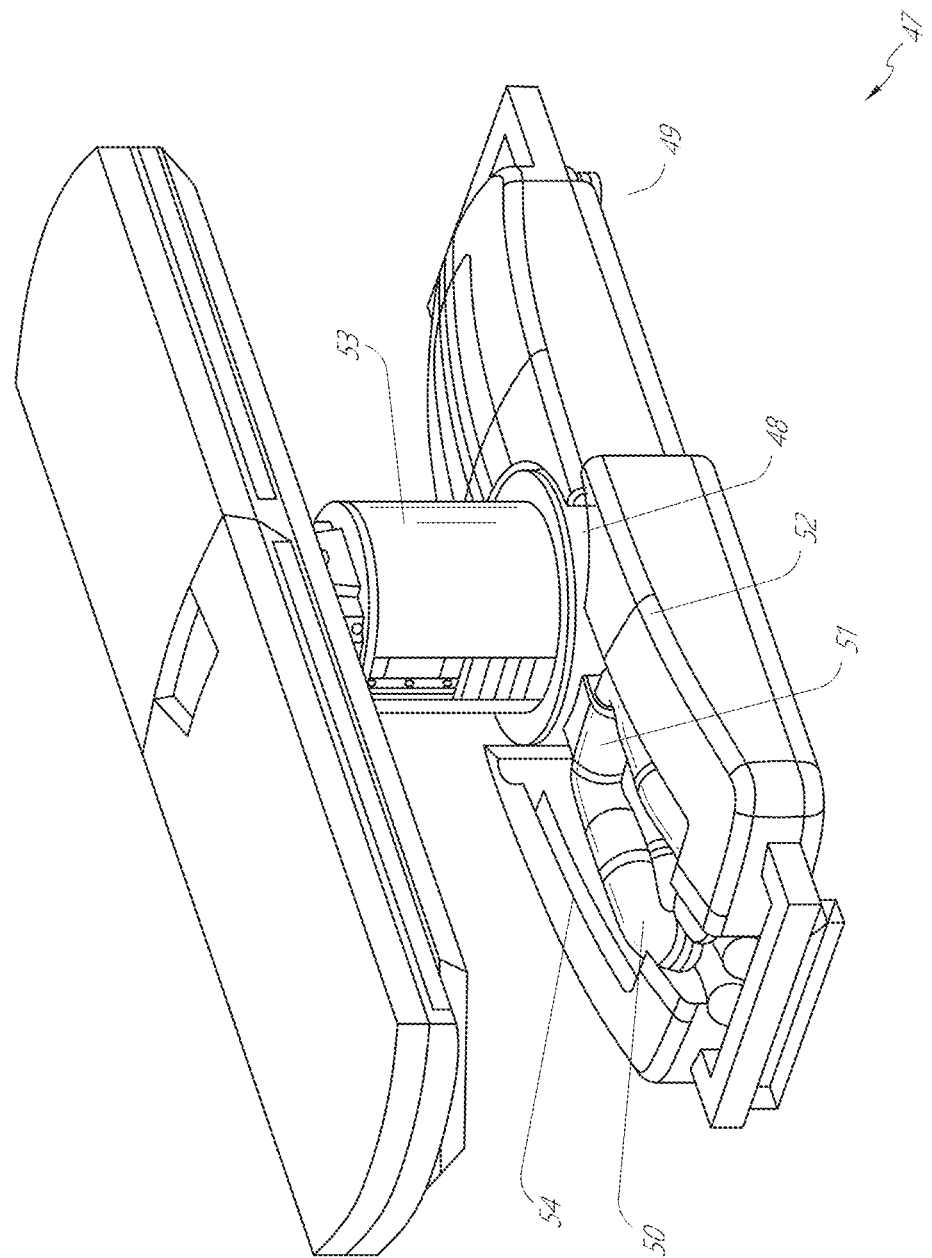
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
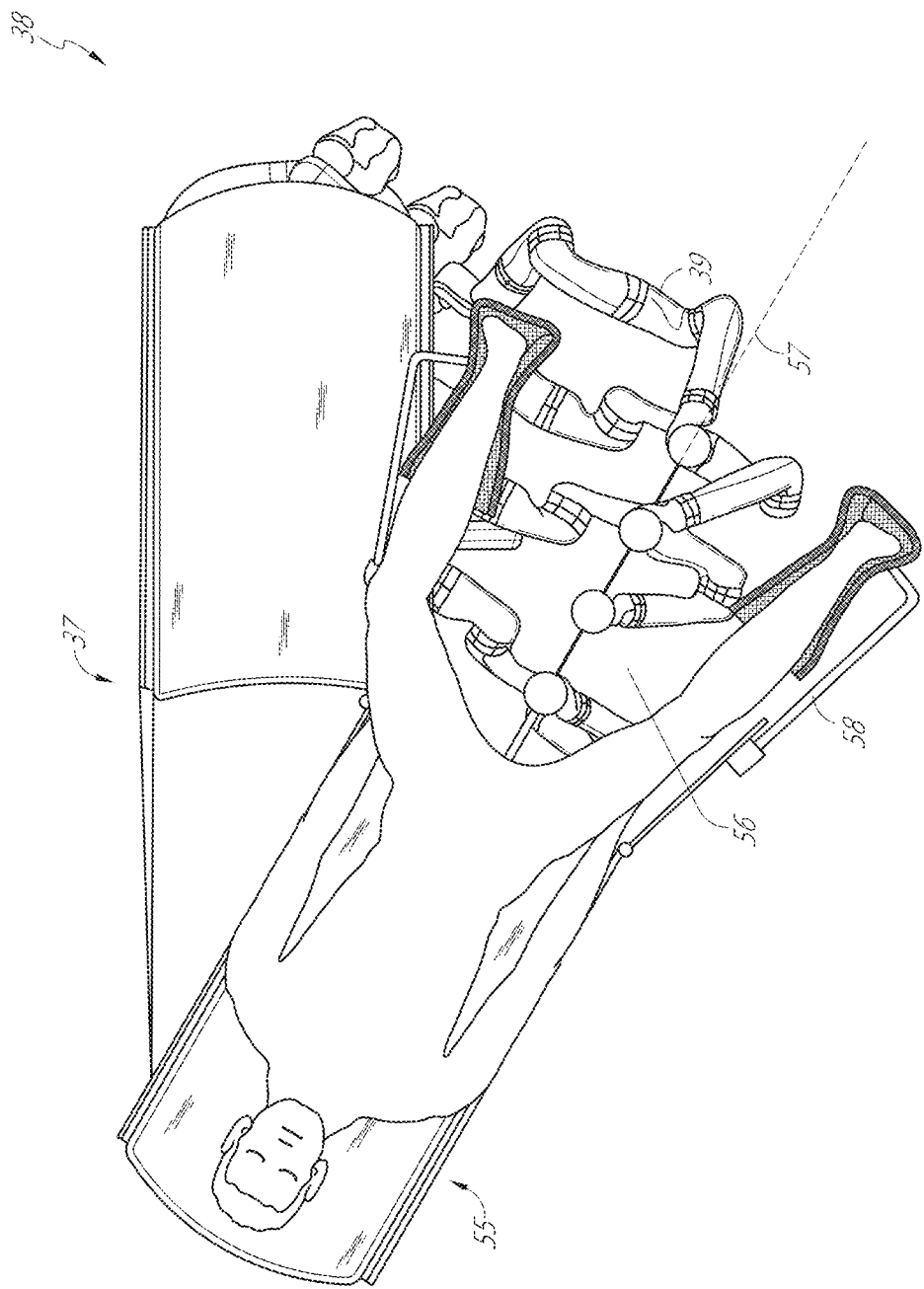
FIG. 8 illustrates an embodiment of a table-based robotic system configured for a ureteroscopy procedure.

FIG. 8 illustrates an embodiment of a robotically-enabled table-based system configured for a ureteroscopy procedure. In ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
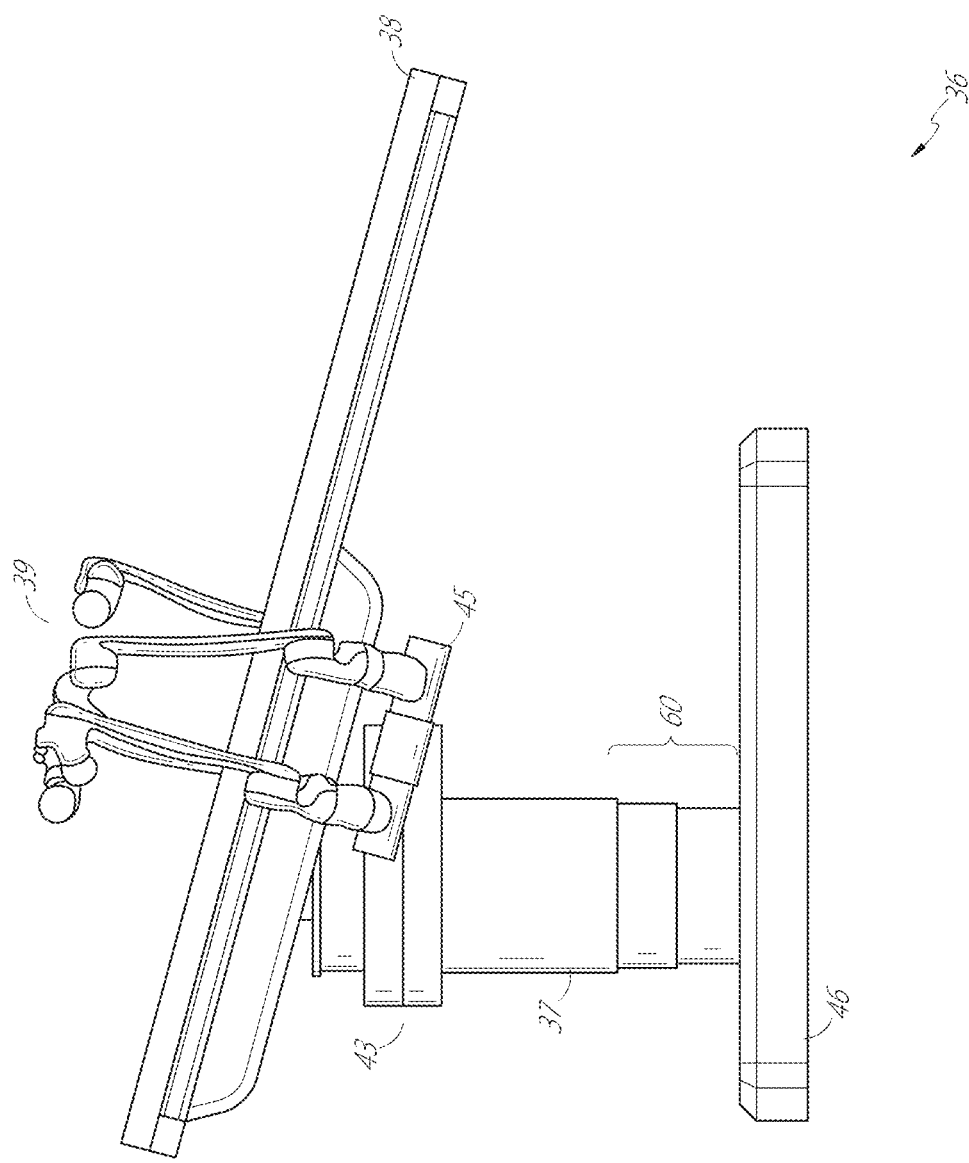
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
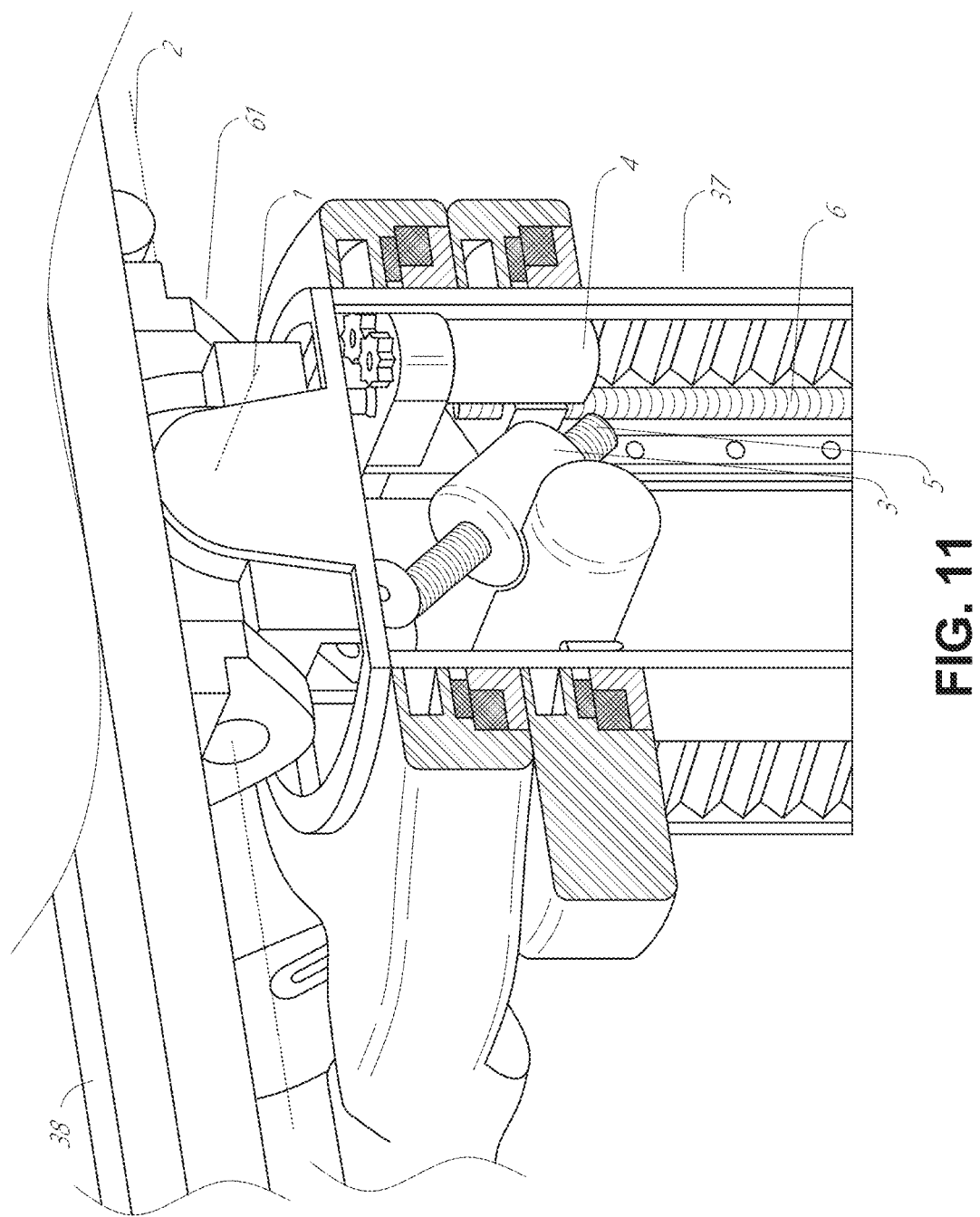
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
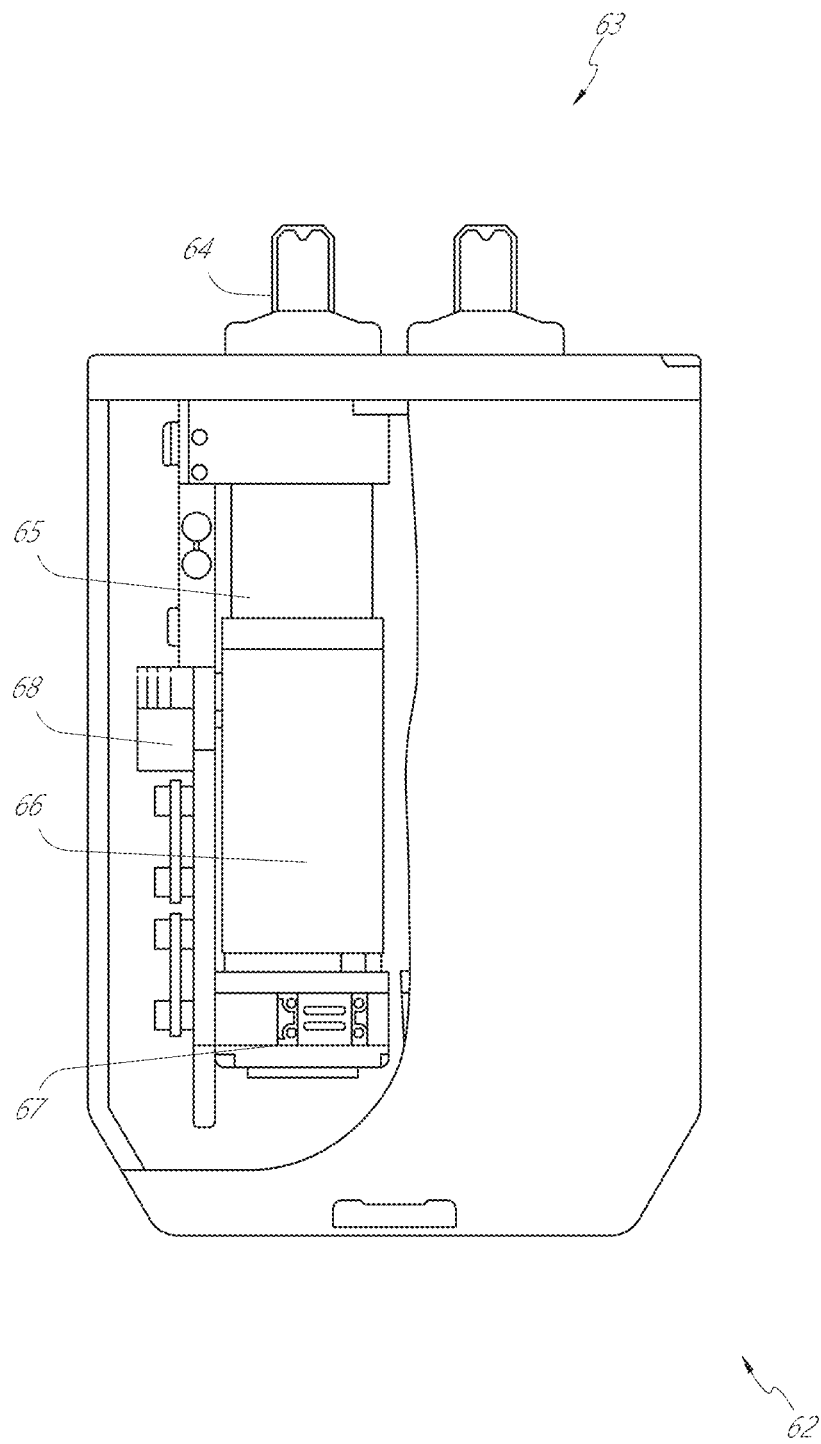
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
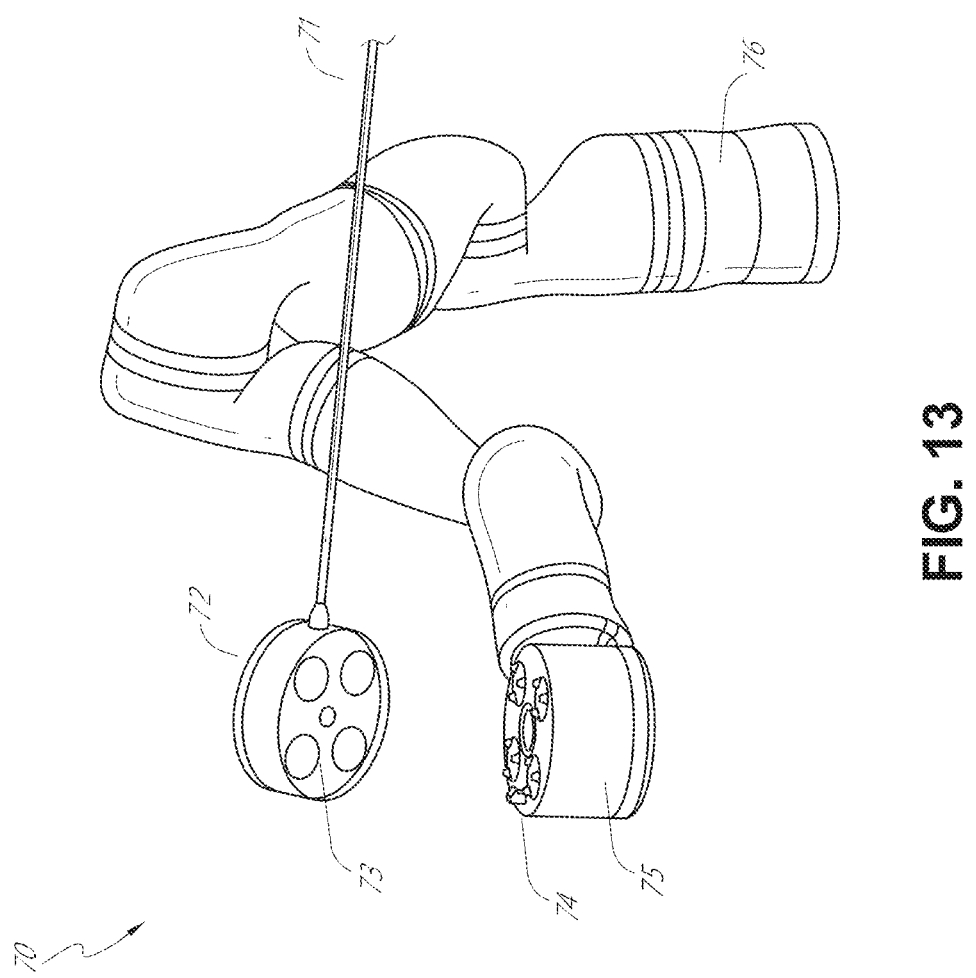
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
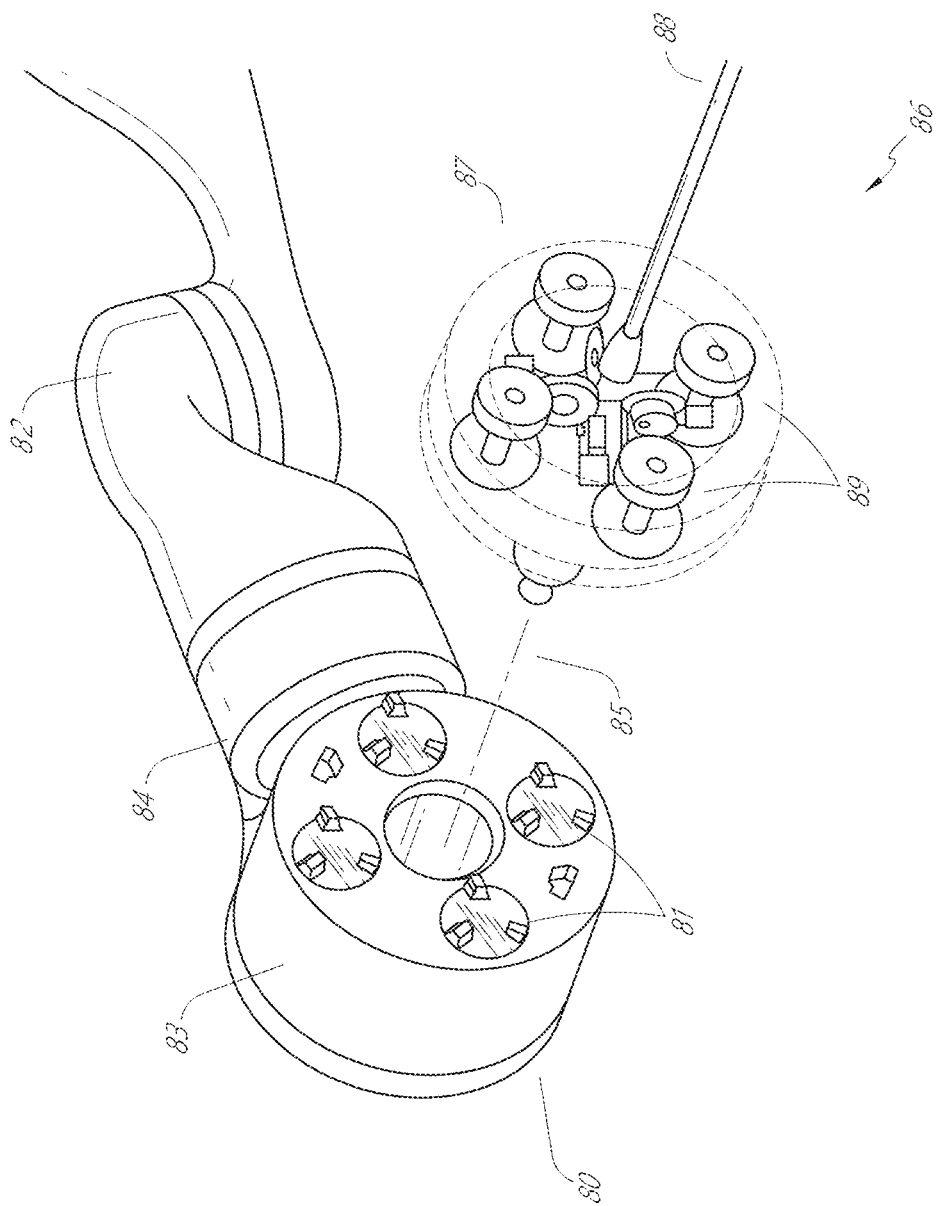
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
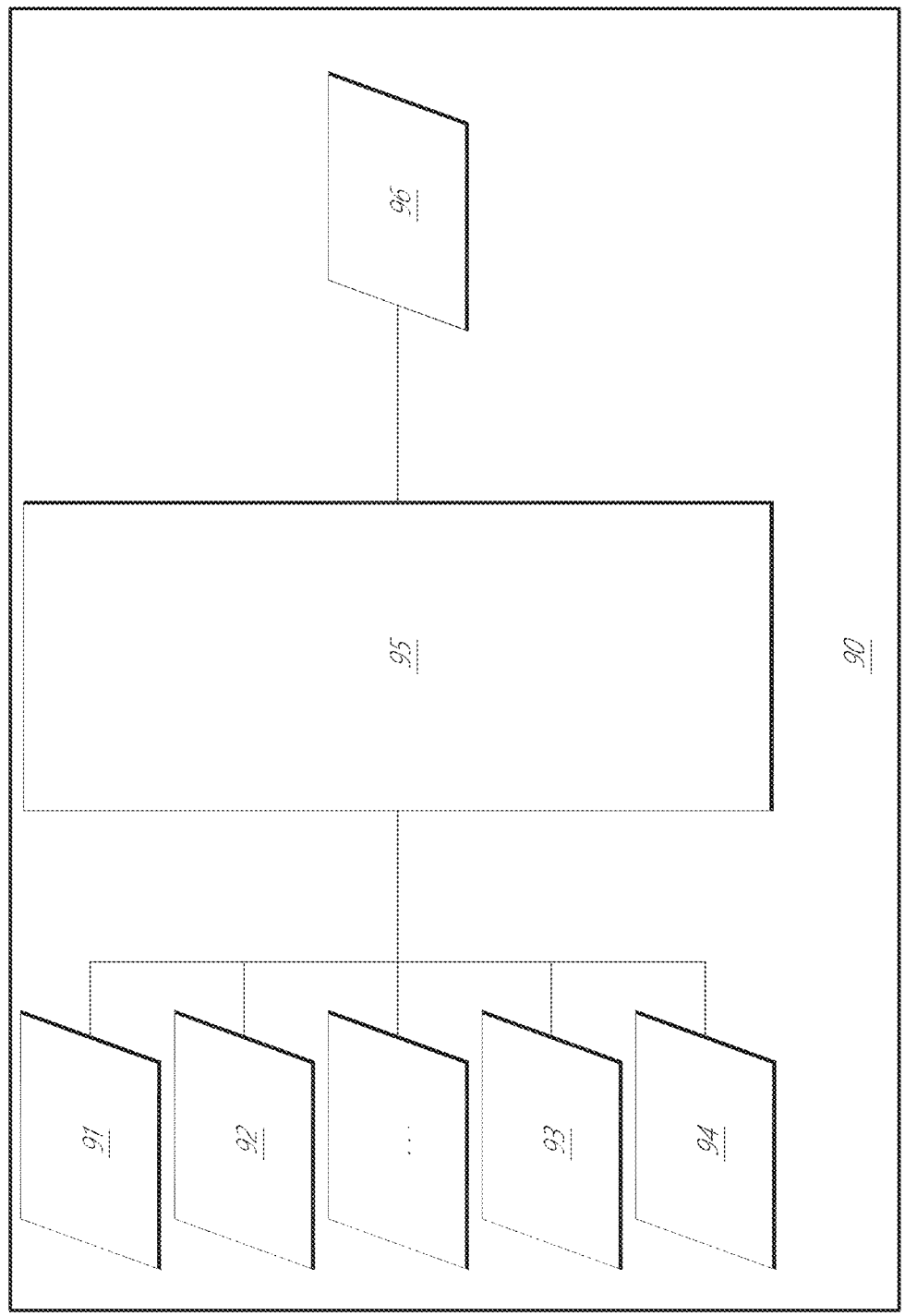
FIG. 15 depicts a block diagram illustrating a localization system that estimates a location of one or more elements of the robotic systems of FIGS. 1-10, such as the location of the instrument of FIGS. 13-14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Uncommanded Instrument Roll Correction

Embodiments of the disclosure relate to systems and techniques that can be used to correct for uncommanded instrument movement, which in certain embodiments involve correcting uncommanded instrument roll. When an operator (e.g., a physician, a surgeon, a bronchoscopist, or a robotic control system) controls a flexible tubular instrument inside the patient's body, the instrument may move in a manner that changes the orientation of the instrument. For example, the instrument may roll or rotate (e.g., with respect to a longitudinal axis of the instrument) independent of the operator's command(s). Such uncommanded movement may occur in various situations such as, for example, when a flexible tubular instrument is inserted through an endotracheal tube and/or when the instrument passes through a curved anatomical structure and conforms its shape to the structure. This uncommanded roll can pose one or more coordination problems for the operator of the flexible tubular instrument because the uncommanded roll may render a visual frame of reference and/or a control frame of reference inconsistent with what the operator desires or expects. Certain embodiments disclosed herein are related to methods and systems for correcting for such unintended instrument movement.

Figure 16:
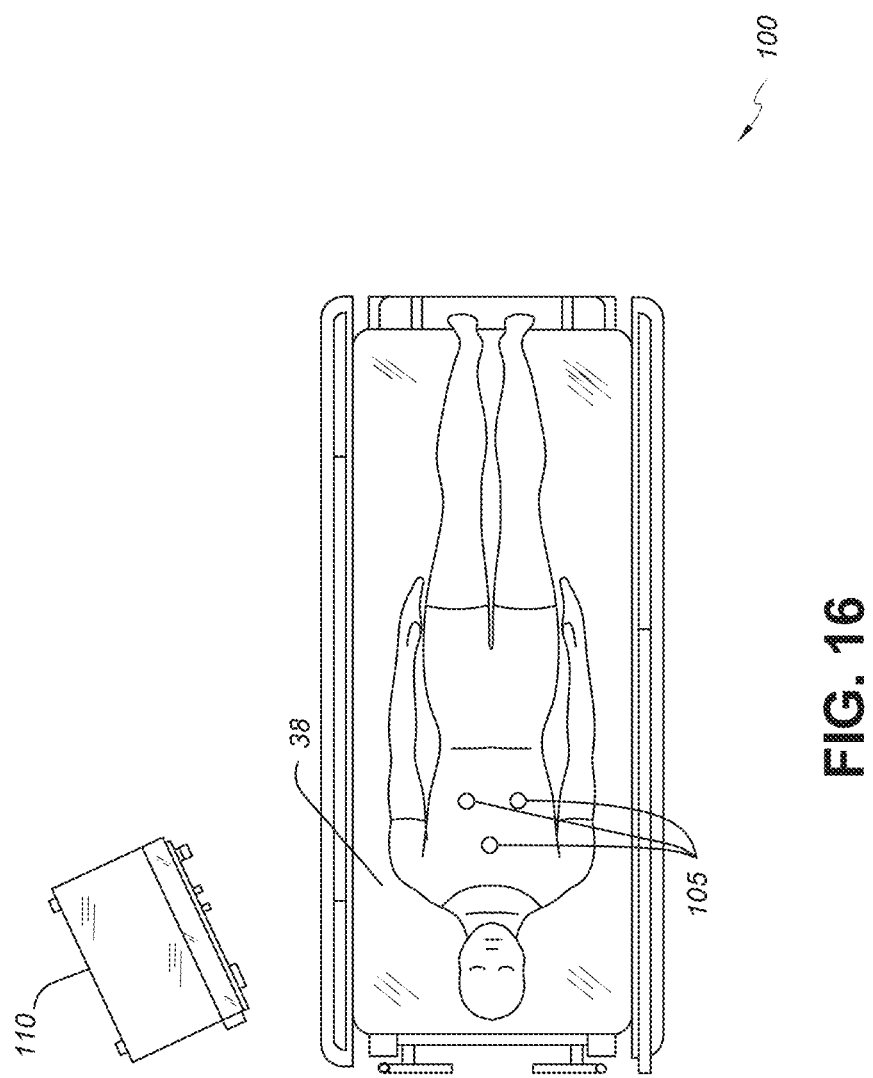
FIG. 16 illustrates an example operating environment implementing one or more aspects of the disclosed systems and techniques.

As discussed above, electromagnetic (EM) data may be used by embodiments discussed herein for navigation and localization of a medical instrument (e.g., a steerable instrument). EM data may be generated by one or more EM sensors located within the medical instrument and/or one or more EM patch sensors placed on a patient. FIG. 16 illustrates an example operating environment 100 implementing one or more aspects of the disclosed systems and techniques to detect and/or correct for uncommanded roll using EM data. The operating environment 100 includes a table 38 supporting a patient, EM sensors 105 (also referred to as "EM patch sensors" so as to be distinguished from EM instrument sensors located on a medical instrument as discussed below), and an EM field generator 110. Additional devices/elements may also be included, but have not been illustrated in FIG. 16. For example, the environment 100 may also include: a robotic system configured to guide movement of a medical instrument, a command center or console for controlling operations of the robotic system, and an EM controller, among others. The EM controller may be electrically connected to EM patch sensors 105 to receive EM sensor signals therefrom. The EM controller may further be connected to the EM field generator 110 to provide control signals thereto for generating the EM field. In certain embodiments, the EM controller may be partially or completely incorporated into one or more of the other processing device of the system, including the EM field generator 110, the cart 11 (see FIG. 1), and/or the tower 30 (see FIG. 1).

When included, the EM controller may control EM field generator 110 to produce a varying EM field. The EM field may be time-varying and/or spatially varying, depending upon the embodiment. The EM field generator 110 may be located on a cart, similar to the cart 11 illustrated in FIG. 2, or may be attached to a rail of the table 38 via one or more supporting columns. In other embodiments, an EM field generator 110 may be mounted on a robotic arm, for example similar to those shown in surgical robotic system 10 of FIG. 1, which can offer flexible setup options around the patient. The EM field generator 110 may have an associated working volume in which the EM patch sensors 105 may be placed when in use.

Figure 18:
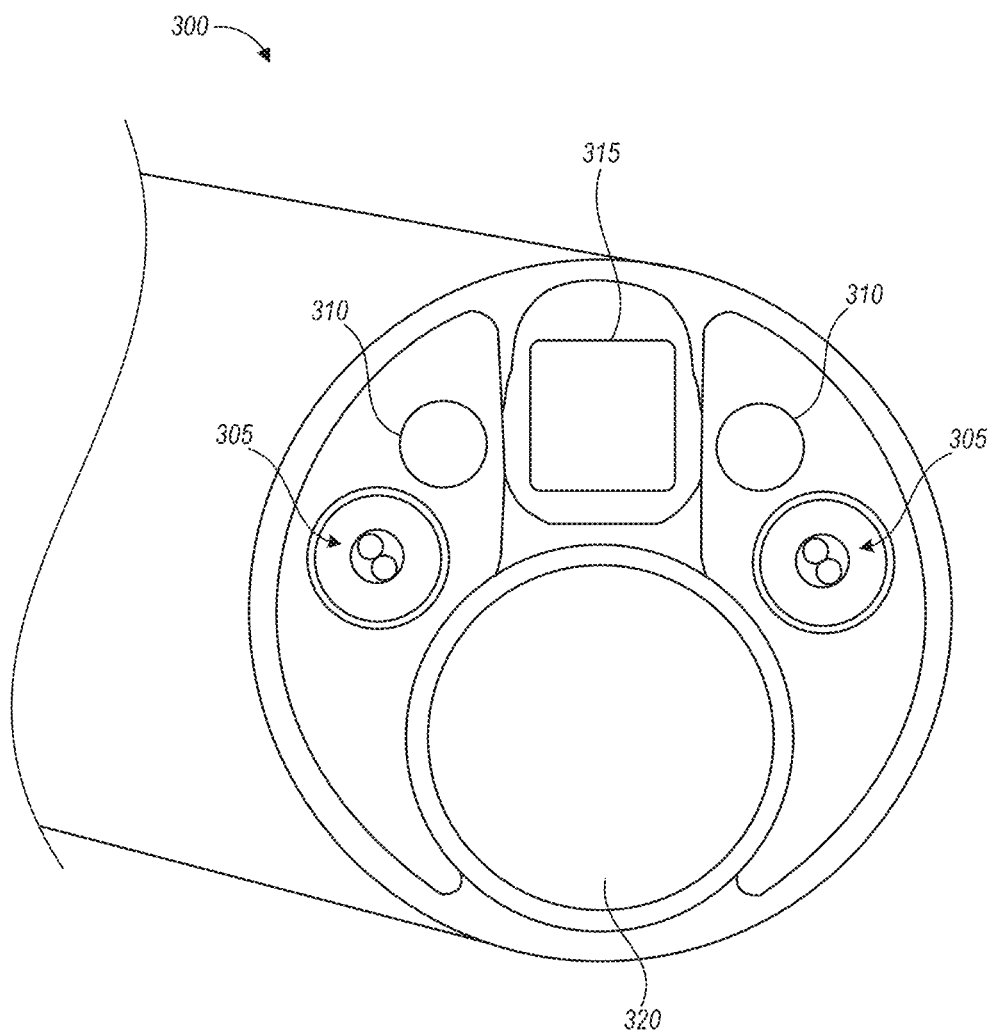
FIG. 18 illustrates a distal end of an exemplary instrument having imaging and EM sensing capabilities.

An EM spatial measurement system may determine the location of objects within the EM field that are embedded or provided with EM sensor coils, for example, EM patch sensors 105 (as shown in FIG. 16) or EM instrument sensors 305 (as shown in FIG. 18 below). When an EM sensor is placed inside a controlled, varying EM field as described herein, voltages are induced in sensor coil(s) included in the EM sensor. These induced voltages can be used by the EM spatial measurement system to calculate the position and orientation of the EM sensor and thus the object having the EM sensor. As the EM fields are of a low field strength and can safely pass through human tissue, location measurement of an object is possible without the line-of-sight constraints of an optical spatial measurement system. The EM field may be defined relative to a coordinate frame of the EM field generator 110, and a coordinate frame of a 3D model of the luminal network can be mapped or registered to the coordinate frame of the EM field. The EM spatial measurement system may be implemented in a robotically controlled system (e.g., system 10, 36 or 47), an instrument driver (e.g., instrument driver 62), a controller (e.g., control circuitry 68), a console (e.g., console 16 or 31), and/or a console base (e.g., cart base 15), or component(s) thereof.

Figure 17:
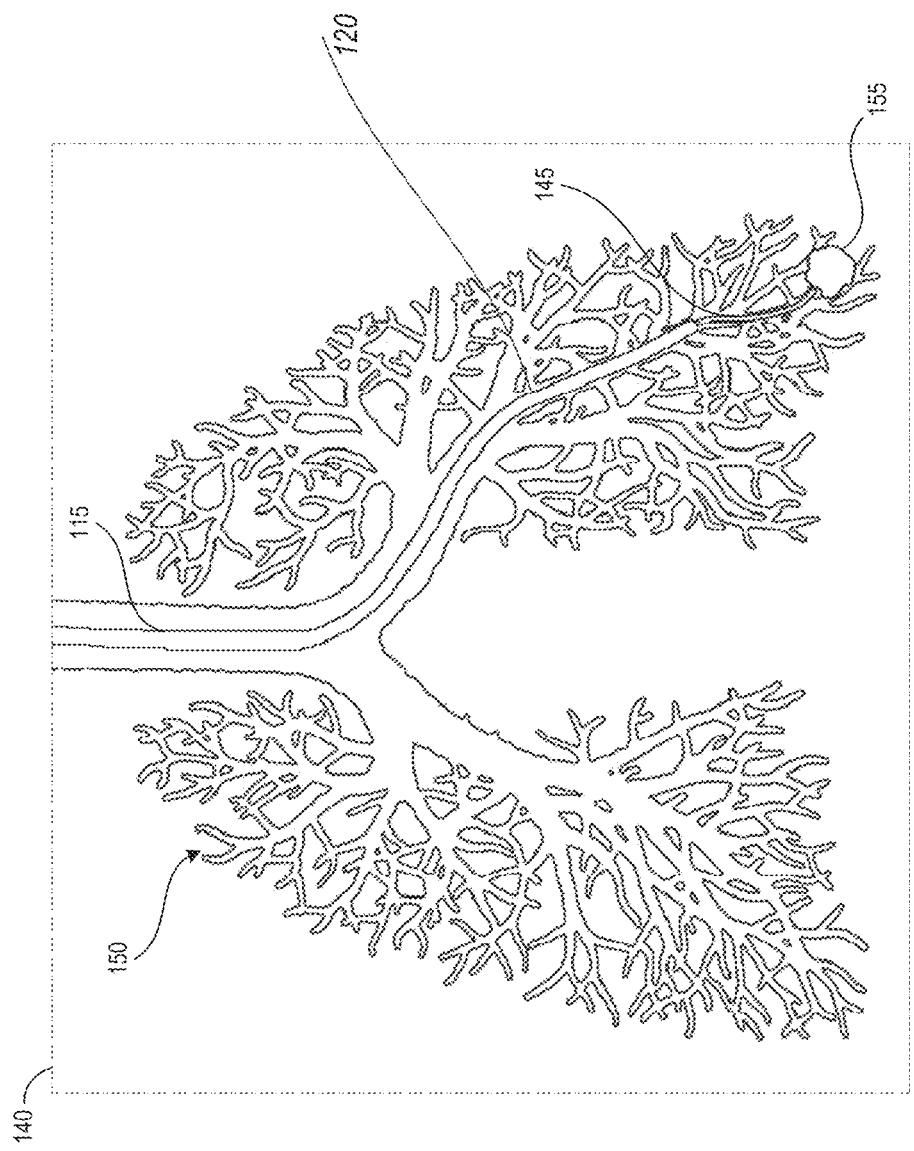
FIG. 17 illustrates an example luminal network that can be navigated in the operating environment of FIG. 16.

As shown in FIG. 16, a number of EM patch sensors 105 may be placed on or near the body of the patient (e.g., in the region of a luminal network 140, see FIG. 17). A number of different EM patch sensors 105 may be spaced apart on the body surface in order to track the different displacements at these locations. For example, the periphery of the lungs may exhibit greater motion due to respiration than the central airways, and providing a number of EM patch sensors 105 as shown can enable more precise analysis of these motion effects. This may allow for accurate tracking of the distal end of an endoscope that may travel through different regions of the luminal network 140 and thus experience varying levels of displacement due to patient respiration as it travels through these different regions.

The EM sensor signals received from the EM patch sensors 105 may be used to determine the positions and orientations of the EM patch sensors 105 with respect to the EM field generator 110. The EM patch sensors 105 may provide 5 degrees-of-freedom (DoF) data for each of the patch sensors (e.g., 3 positional DoF and 2 angular DoF) or 6 DoF data (e.g., 3 positional DoF and 3 angular DoF).

FIG. 17 illustrates an example luminal network 140 that can be navigated in, for example, the operating environment 100 of FIG. 16. As illustrated, the luminal network 140 includes a branched structure of airways 150 of the patient and a nodule 155 that can be accessed as described herein for diagnosis and/or treatment. In this example, the nodule 155 is located at a periphery of the airways 150. An endoscope 115 may comprise a sheath 120 and a leader 145. In one embodiment, the sheath 120 and the leader 145 may arranged in a telescopic manner. For example, the leader 145 may be slidably positioned inside a working channel of the sheath 120. The sheath 120 can have a first diameter, and its distal end may not be able to be positioned through the smaller-diameter airways 150 around the nodule 155. Accordingly, the leader 145 can be configured to extend from the working channel of the sheath 120 the remaining distance to the nodule 155. The leader 145 may have a lumen through which instruments, for example biopsy needles, cytology brushes, and/or tissue sampling forceps, can be passed to the target tissue site of the nodule 155. In such implementations, both the distal end of the sheath 120 and the distal end of the leader 145 can be provided with EM instrument sensors (e.g., EM instrument sensors 305 in FIG. 18) for tracking their position within the airways 150. This telescopic arrangement of the sheath 120 and the leader 145 may, in some embodiments, allow for a thinner design of the endoscope 115 and may improve a bend radius of the endoscope 115 while providing a structural support via the sheath 120.

In other embodiments, the overall diameter of the endoscope 115 may be small enough to reach the periphery without the telescopic arrangement, or may be small enough to get close to the periphery (e.g., within 2.5-3 cm) to deploy medical instruments through a non-steerable catheter. The medical instruments deployed through the endoscope 115 may be equipped with EM instrument sensors (e.g., EM instrument sensors 305 in FIG. 18), and the position filtering and safety-mode navigation techniques described below can be applied to such medical instruments. In some embodiments, a 2D display of a 3D luminal network model as described herein, or a cross-section of a 3D model, can resemble FIG. 17. In some embodiments, navigation safety zones and/or navigation path information can be overlaid onto such a representation.

FIG. 18 illustrates the distal end 300 of an example instrument (e.g., endoscope 115, sheath 120, or leader 145 of FIG. 17, and/or medical instrument 70 or endoscope 13 of FIG. 1) that can include imaging and EM sensing capabilities as described herein. However, aspects of this disclosure may relate to the use of other steerable instruments, such as ureteroscope 32 of FIG. 3, laparoscope 59 of FIG. 9, etc. As shown in FIG. 18, the distal end 300 of the instrument can include an imaging device 315, illumination sources 310, and ends of coils of EM sensors 305. The distal end 300 can further include an opening to a working channel 320 of the instrument through which tools (e.g., biopsy needles, cytology brushes, and forceps) may be inserted along the instrument shaft, allowing access to the area near the distal end 300 of the instrument.

The illumination sources 310 can provide light to illuminate a portion of an anatomical space. The illumination sources can each be one or more light-emitting devices configured to emit light at a selected wavelength or range of wavelengths. The wavelengths can be any suitable wavelength, for example visible spectrum light, infrared light, x-ray (e.g., for fluoroscopy), to name a few examples. In some embodiments, illumination sources 310 can include light-emitting diodes (LEDs) located at or near the distal end 310. In some embodiments, illumination sources 310 can include one or more fiber optic fibers extending through a length of the endoscope to transmit light through the distal end 300 from a remote light source, for example an X-ray generator. Where the distal end 300 includes multiple illumination sources 310 these can each be configured to emit the same or different wavelengths of light.

The imaging device 315 can include any photosensitive substrate or structure configured to convert energy representing received light into electric signals, for example a charge-coupled device (CCD) or complementary metal-oxide semiconductor (CMOS) image sensor. Some examples of imaging device 315 can include one or more optical fibers, for example a fiber optic bundle, configured to transmit an image from the distal end 300 of the endoscope to an eyepiece and/or image sensor at the proximal end of the endoscope. Imaging device 315 can additionally include one or more lenses and/or wavelength pass or cutoff filters as required for various optical designs. The light emitted from the illumination sources 310 allows the imaging device 315 to capture images of the interior of a patient's luminal network. These images can then be transmitted as individual frames or series of successive frames (e.g., a video) to a computer system such as a command console for processing and/or display.

EM sensors 305 located on the distal end 300 can be used with an EM tracking system to detect the position and/or orientation of the distal end 300 of the endoscope while it is positioned within an anatomical system. In some embodiments, the EM sensors 305 may be angled to provide sensitivity to EM fields along different axes, giving the disclosed navigational systems the ability to measure a full 6 DoF: three positional DoF and three angular DoF. In other embodiments, only a single coil or sensor may be disposed on or within the distal end 300 with its axis oriented along the endoscope shaft of the endoscope. When only a single EM coil or sensor is placed on the distal end 300 of the instrument, rendering the system symmetric with respect to its axis (e.g., its longitudinal axis), the system may not detect one or more rolls with respect to its axis because such roll(s) do not change magnetic flux or electric flux across the single coil or sensor. Due to the rotational symmetry of such a system, it may be insensitive to roll about its axis, so only 5 DoF may be detected in such an implementation. The system may be sensitive to roll(s) with respect to its axis when the system comprises two or more coils or sensors having symmetry axes that are not parallel, (e.g., symmetry axes that are perpendicular to one another). For the system with one or more EM coils or sensors not sensitive to roll(s) with respect to its axis, the uncommanded roll may be detected via one or more sensors or detectors other than EM coils. In some embodiments, the uncommanded roll may be determined by analyzing one or more images from an imaging device (e.g., the imaging device 315 or imaging device at or near the distal end of the instrument).

Figure 19A:
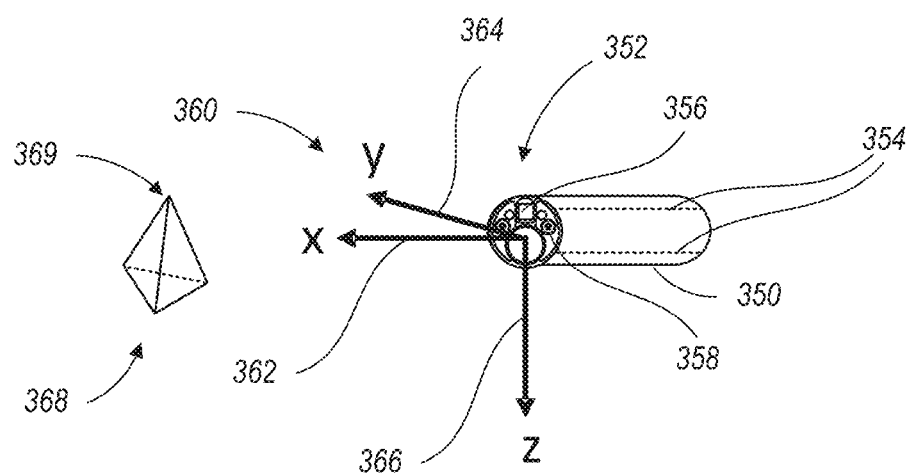
FIGS. 19A-19B illustrates a tip frame of reference, a visual frame reference, a control frame reference, and a desired frame of reference of an example medical instrument
Figure 19B:
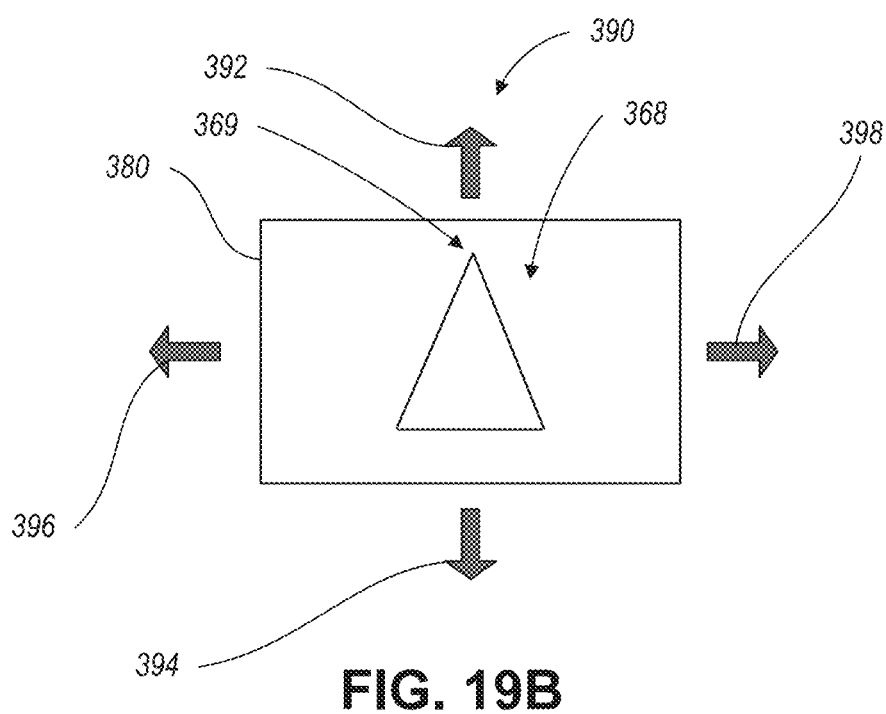

FIGS. 19A-19B illustrate a tip frame of reference, a visual frame reference, a control frame reference, and a desired frame of reference of an example medical instrument (e.g., medical instrument 350, medical instrument 70 or endoscope 13 of FIG. 1). FIG. 19A shows a tip frame of reference 360 and a desired frame of reference 368 of a medical instrument 350 in a three dimensional (3D) space. The medical instrument 350 has a distal tip 352 that comprises one or more components similar to those of the distal end 300 of the medical instrument shown in FIG. 18 (e.g., imaging device 356 and/or EM sensor coils 358). The medical instrument 350 may also comprise one or more pullwires 354 configured to manipulate or articulate the distal tip 352 of the instrument 350. The tip frame of reference 360 may represent an orientation of the distal end 352 of the instrument 350. The tip frame of reference 360 comprises the x-axis 362, the y-axis 364, and the z-axis 366. As will be explained in greater detail below, the tip frame of reference 360 may be determined by one or more imaging devices (e.g., imaging device 356), location sensors (e.g., EM patch sensors 105), EM coils (e.g., EM sensor coils 358), any other suitable sensor (e.g., an accelerometer measuring the force of gravity or other motions of the instrument 350), or combinations thereof.

The desired frame of reference 368 can be a frame of reference on which an adjustment to the visual frame of reference and/or the control frame of reference is based. In some embodiments, the desired frame of reference 368 may be a target frame of reference to which a system or an operator aims to transform the visual frame of reference and/or the control frame of reference. The system can cause this transformation to execute based on a trigger—such as a request (as may be initiated and received from a user input)—or the system can cause this transformation to execute on an ongoing basis so that a consistent view and control is maintained during a medical procedure. The desired frame of reference 368 may be an anatomical frame of reference (e.g., a frame of reference determined by an anatomical feature) or a world frame of reference (e.g., a frame of reference determined by the direction of gravity). In FIG. 19A, the desired frame of reference 368 is represented by a triangular pyramid with an apex 369 pointing at a reference direction (e.g., an up direction or a z-direction).

FIG. 19B illustrates the desired frame of reference 368, the visual frame of reference 380, and the control frame of reference 390 of the medical instrument 350 as shown in one or more images from the imaging device 356 at the distal end 352 of the medical instrument 350. The visual frame of reference 380 represents an orientation of an output image generated from an image captured from the imaging device 356 of the medical device 350. In FIG. 19B, the visual frame of reference 380 is aligned to the desired frame of reference 368, represented by the triangular pyramid shown in the visual frame of reference 380. In other words, the apex 369 of the triangular pyramid representing the up direction corresponds to the up direction of the visual frame of reference 380. It is to be noted, and is explained further below, that the visual frame of reference 380 may be adjusted based on changes to the tip frame of reference 360 in such a way that the output image is consistent with the desired frame of reference 368 despite changes to the tip frame of reference 360, as may be experienced during an uncommanded roll.

The control frame of reference 390 is data that represents a relationship between a motor control command and a motor output of the instrument 350. In FIG. 19B, the control frame of reference 390 is represented by control frame indicators 392, 394, 396, and 398. It is to be appreciated that the control frame indicators 392, 394, 396, and 398 are shown merely to illustrate the direction of movement in which a control input will cause the medical device 350 to actuate. For example, pressing the up direction on the user input device will cause the tip of the medical device 350 to actuate up in a manner represented by control frame indicator 392. In some embodiments, the control frame indicators 392, 394, 396, and 398 may be displayed on the screen. In those embodiments, the control frame indicators 392, 394, 396, and 398 may comprise one or more shapes (e.g., arrows, dots, or triangles) representing directions toward which an operator (e.g., a physician, a surgeon, a bronchoscopist, or a robotic control system) may command the medical instrument 350 to move (e.g., up, down, left, and right, respectively). Similar to the visual frame of reference 380, it is to be noted, and is explained further below, that the control frame of reference 390 may be adjusted based on changes to the tip frame of reference 360 in such a way that a motor control command is consistent with the desired frame of reference 368 despite changes to the tip frame of reference 360, as may be experienced during an uncommanded roll.

Figure 20A:
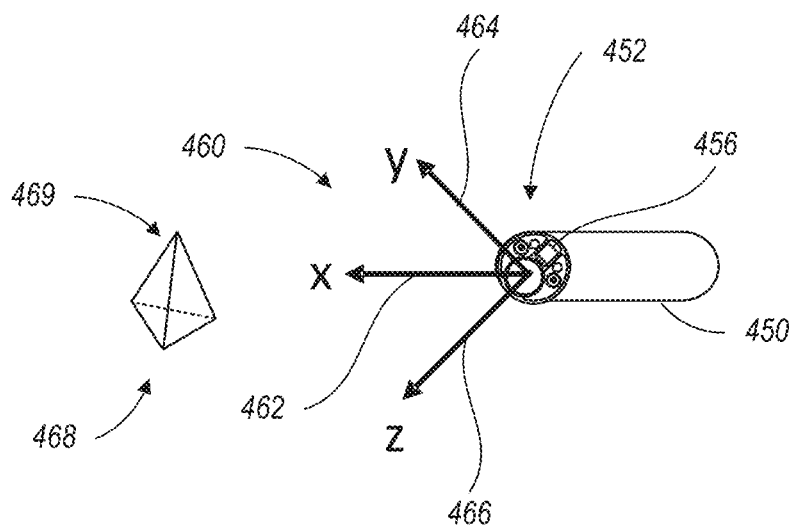
FIGS. 20A-20B illustrate a tip frame of reference, a visual frame reference, a control frame reference, and a desired frame of reference of an example medical instrument with uncommanded instrument roll.
Figure 20B:
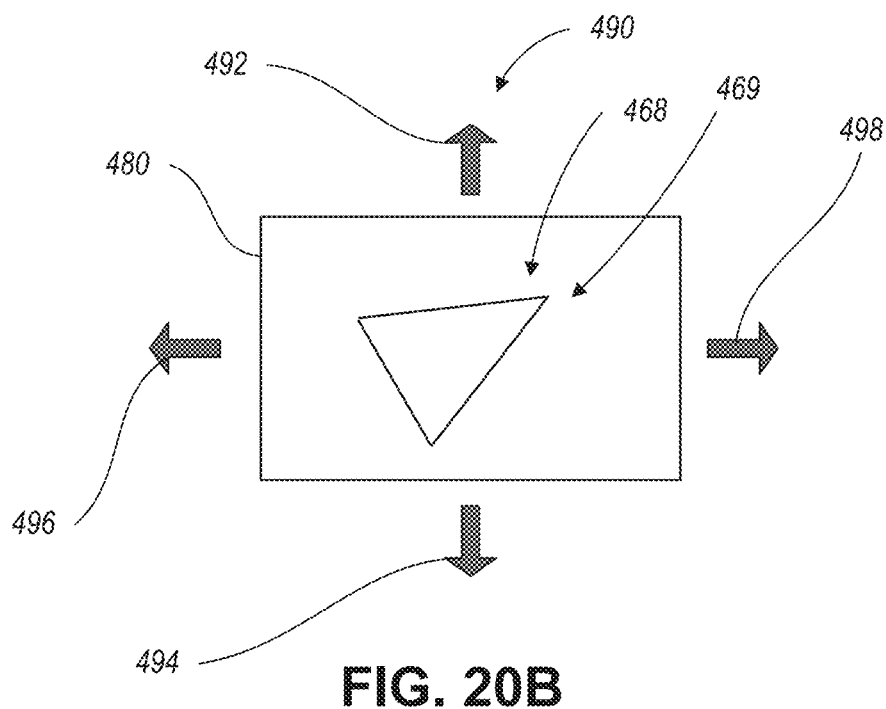

FIGS. 20A-20B illustrate changes in a tip frame of reference 460, a visual frame reference 480, a control frame reference 490, and a desired frame of reference 468 of an example medical instrument (e.g., medical instrument 450). FIG. 20A shows the tip frame of reference 460 and the desired frame of reference 468 of the medical instrument 450 in a 3D space after an occurrence of an uncommanded roll but without any correction. In the illustrated example, a distal tip 452 of the medical instrument 450 shows that the distal tip 452 is oriented diagonally due to the uncommanded roll. Accordingly, the tip frame of reference 460, which comprises the x-axis 462, the y-axis 464, and the z-axis 466, is also oriented in a diagonal direction. The desired frame of reference 468 is represented by a triangular pyramid with an apex 469 pointing upward.

FIG. 20B illustrates the desired frame of reference 468, the visual frame of reference 480, and the control frame of reference 490 of the medical instrument 450 as shown in one or more images from the imaging device 456 at the distal end 452 of the medical instrument 450 based on the uncommanded roll illustrated in FIG. 20A, again without any correction. As shown in FIG. 20B, the visual frame of reference 480, and the control frame of reference 490 (represented by the control frame indicators 492, 494, 496, and 498) of the medical instrument 450 are not consistent with the desired frame of reference 368. Such inconsistencies may result in a disorienting experience for the end-user. For example, without commanding a roll, the images displayed by the medical device will be at an orientation inconsistent with the end-user's expectation. As can be seen in this example, the control frame indicator 492 (which, in some embodiments, operators anticipate will be an upward direction) is not aligned with the upward direction of the desired frame of reference 468 (as indicated by the apex 469) due to the uncommanded roll of the medical instrument 450.

Figure 21A:
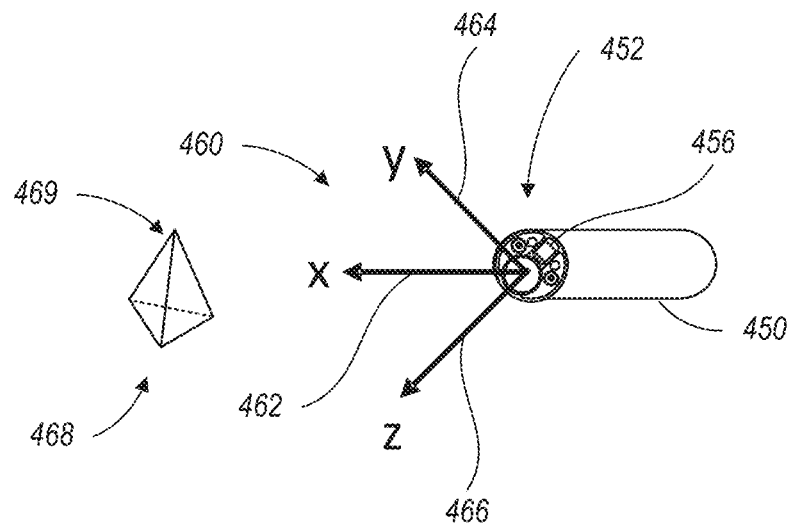
FIGS. 21A-21B illustrate a tip frame of reference, a visual frame reference, a control frame reference, and a desired frame of reference of the example medical instrument of FIGS. 20A-20B after a correction for uncommanded instrument roll.
Figure 21B:
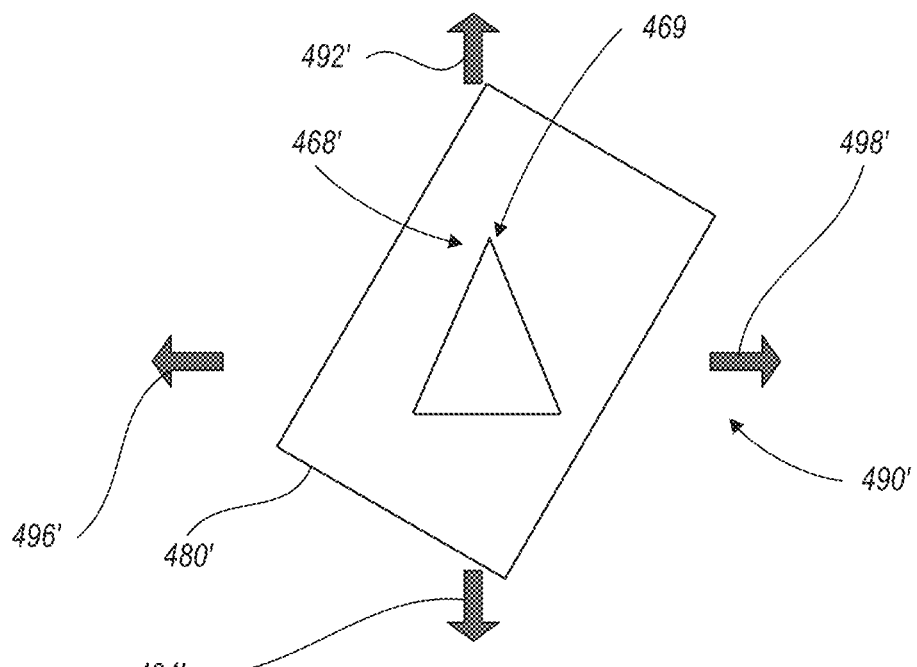

In contrast with FIGS. 20A-20B, FIGS. 21A-21B illustrate the tip frame of reference 460', the visual frame reference 480', the control frame reference 490', and a desired frame of reference 468' of an example medical instrument (e.g., medical instrument 450) after a correction for an uncommanded roll. FIG. 21A shows the tip frame of reference 460 (represented by the x-axis 462, the y-axis 464, and the z-axis 466) and the desired frame of reference 468 of the medical instrument 450 in a 3D space. The correction for an uncommanded roll may comprise one or more adjustments to the visual frame of reference 480 and the control frame of reference 468, which will be described below, and, in some embodiments, the adjustments to the visual frame of reference 480 and the control frame of reference 490 may occur without change(s) in the tip frame of reference 460. FIG. 20B illustrates the desired frame of reference 468', the visual frame of reference 480', and the control frame of reference 490' of the medical instrument 450 (represented by the control frame indicators 492', 494', 496', and 498') as shown in one or more images from the imaging device 456 at the distal end 452 of the medical instrument 450 after the uncommanded roll correction. During the adjustment, the visual frame of reference 480' and the control frame of reference 490' of the medical instrument 450 are rotated such that the apex 469 of the triangular pyramid representing the desired frame of reference 468' is displayed so that the apex 469 points upward, and the control frame indicators 492', 494', 496', and 498' continue to represent the up, down, left, and right directions, respectively, with respect to the desired frame of reference 468'. This adjustment may assist in nimble and consistent manipulation of the medical instrument 450 by the operator by, for example, orienting the visual frame reference 480' and the control frame reference 490' in a direction that is intuitive to the operator. One or more methods to adjust or transform the visual frame of reference and/or the control frame of reference based on the tip frame of reference and/or the desired frame of reference is further described below.

Figure 22:
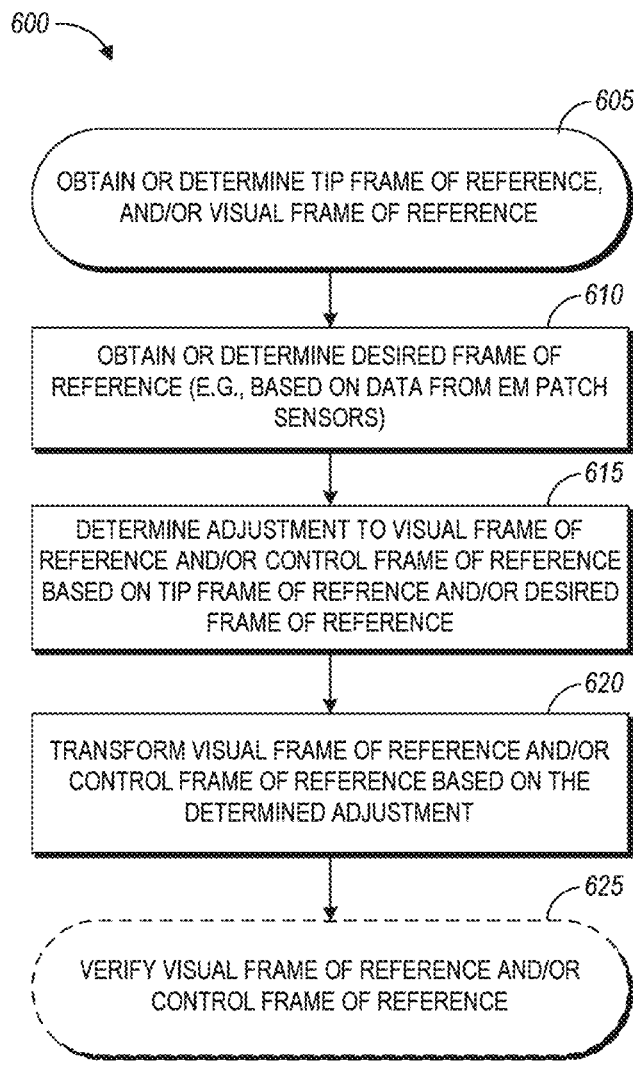
FIG. 22 depicts a block diagram illustrating an exemplary process for correcting for uncommanded instrument roll.

In accordance with one or more aspects of the present disclosure, FIG. 22 depicts a flowchart of an example method or process 600 for correcting for uncommanded instrument roll as described herein. As described herein, the process 600 may be used to adjust or transform a visual frame of reference and/or a control frame of reference based on the tip frame of reference and/or the desired frame of reference so that control of the instrument is more intuitive. For example, the process 600 may align the visual frame of reference and/or the control frame of reference with the directions anticipated or expected by the user, regardless of uncommanded roll of the instrument of the position of the tip frame of reference. The process 600 can be implemented, for example, in a robotically controlled system (e.g., system 10, 36 or 47), an instrument driver (e.g., instrument driver 62), a controller (e.g. control circuitry 68), a console (e.g., console 16 or 31), and/or a console base (e.g., cart base 15), or component(s) thereof. Thus, the system implementing the process 600 described below is not limited to a robotically controlled system. In some cases, one or more blocks of the example process 600 may be performed by a user of the system.

The process 600 may begin at block 605. At block 605, the system may obtain or determine a tip frame of reference (e.g., tip frame of reference 360 in FIG. 19A or tip frame of reference 460 in FIGS. 20A and 21A) of a medical instrument (e.g., medical instrument 150, 350, or 450). As described above in FIGS. 19A-21B, the tip frame of reference may represent a physical orientation of a distal end of the medical instrument. In some aspects, the system may be configured to obtain the tip frame of reference from, for example, the one or more sensors on the medical instrument. For example, the system may be configured to obtain data from one or more imaging devices, location sensors, or EM coils or sensors and to calculate the tip frame of reference based on the data. In a vision-based example, the tip frame of reference may be determined by analyzing one or more images (e.g., one or more images from the imaging device). During the analysis of the images, one or more anatomical features of the patient may be used to determine the tip frame of reference. As is explained further below, the anatomical features can be features that characterize features shown in intraoperative image data. In a positional based example, the tip frame of reference may be determined based data from a location sensor on the medical instrument and EM patch sensors attached to the patient or equipment located near the patient (e.g., the operating bed).

At block 610, the system may obtain or determine a desired frame of reference (e.g., desired frame of reference 368 or 468). Similar to obtaining the tip frame of reference, the desired frame of reference may be determined based an anatomical frame of reference (e.g., based on the anatomy of the patient), a world frame of reference (e.g., based on a feature of the world, such as the direction of gravity), or the like. Other embodiments may use other frames of reference. In cases where the desired frame of reference is determined from an anatomical frame of reference, the desired frame of reference may be based on one or more anatomical features of the patient derived from preoperative data (e.g., one or more anatomical models) or assumptions on the characteristics of an anatomical feature. For example, prior to the procedure, a model of the patient's anatomy may be generated and processed to determine features of the anatomy to determine the desired frame of reference. Such a feature could be based on the orientation of the center points of the airways at a given location in the model. Additionally or alternatively, rather than using features derived from a model of the patient's anatomy, embodiments may determine a desired frame of reference based on an assumption or known characteristic of the patient's anatomy. One such assumed or known characteristic is the centerlines of the left bronchus and right bronchus in the main carina are substantially aligned in the horizontal axis. An exemplary process for determining a desired frame of reference based on a feature of the anatomy (e.g., derived from preoperative data or assumed/known) of the patient is described below in FIG. 25.

As just mentioned, some embodiments may derive the desired frame of reference from a frame of reference derived from static patch sensors located near the patient (e.g., on the bed or attached to the chest of the patient). In these embodiments, the system can detect the direction of gravity based on, for example, a plane formed by the patch sensors. For example, where the patches are placed on the patient's chest or the bed of the operating table, the negative z-direction of the plane formed by the multiple patches may be assumed to be the direction of gravity. The system may then operate such that the desired frame of reference is relative (e.g., aligned) to the direction of gravity. Some embodiments using patch sensors to determine a desired frame of reference are discussed in greater detail with reference to FIG. 23.

At block 615, the system may determine an adjustment to a visual frame of reference (e.g., visual frame of reference 380 or 480) and/or a control frame of reference (e.g., control frame of reference 390 or 490) based on the current tip frame of reference relative to the desired frame of reference. The adjustment may be determined based on a difference between the tip frame of reference and the desired frame of reference and making corresponding adjustments to the visual frame of reference and/or the control frame of reference. Exemplary adjustment processes in which the adjustments to the visual frame of reference and the control frame of reference are determined based on the desired frame of reference are described in FIGS. 19A-21B and FIGS. 24A-24D.

At block 620, the system may transform the visual frame of reference and/or the control frame of reference based on the determined adjustment. In some embodiments, the system may transform the visual frame of reference and/or the control frame of reference by rotating the visual frame of reference and/or the control frame of reference with respect to a longitudinal axis of the medical instrument. In some embodiments, the system may transform the visual frame of reference and/or the control frame of reference by rotating the visual frame of reference and/or the control frame of reference until it is aligned with the desired frame of reference. In some embodiments, the system may transform the visual frame of reference and/or the control frame of reference based on a user input. In some embodiments, the system may transform the visual frame of reference and/or the control frame of reference by rotating the visual frame of reference and/or the control frame of reference to reduce the effects of roll of the distal end of the instrument or the accumulated roll of the tip frame of reference.

At block 625, the system may further verify the transformed visual frame of reference and/or the transformed control frame of reference. In some embodiments, the system may verify the transformed visual frame of reference and/or the transformed control frame of reference by moving the instrument in one or more directions, calculating or determining an expected change in the visual frame of reference and/or the control frame of reference in response to the movement of the instrument, and comparing an actual change in the visual frame of reference and/or the control frame of reference and the expected change. In some embodiments, moving the instrument in one or more directions may comprise moving the instrument in a particular sequence of movements. In some aspects, a visual motion detection method (e.g., optical flow) may be used to compare between an actual change in the visual frame of reference and/or the control frame of reference and the expected change. In some aspects, the visual motion detection method may check whether an image from the distal end of the instrument moved in the same direction (or the same manner) as the instrument. In some aspects, the system may further adjust the visual frame of reference and/or the control frame of reference based on the comparison. The verification step may be particularly useful when, for example, the instrument roll is greater than 180 degrees.

It is to be appreciated that where the system includes telescoping medical instruments where multiple of the instruments may be articulable, similar adjustments to the visual frame of reference and/or control frame of reference may be made. For example, the determined adjustment made for one instrument may be applied to the other instruments. In some embodiments, individual telescoping instruments may be adjusted independently.

In related aspects, the system may be configured to transform a control frame of the medical instrument configured to be inserted into a patient. The system may comprise a control system configured to determine movement of the medical instrument, at least one computer-readable memory having stored thereon executable instructions, and one or more processors in communication with the at least one computer-readable memory and configured to execute the instructions to cause the system to at least: obtain a control frame of reference representing relationship between a motor control command and a motor output of the medical instrument, determine a tip frame of reference based on data from at least one imaging device (e.g., imaging device 315, 356, or 456) or location sensor (e.g., EM coils 305 or 358, or EM patch sensors 105, 670, 672, or 674) at or near a distal end of the medical instrument, the tip frame of reference representing a current orientation of the distal end of the medical instrument; obtain a desired frame of reference; and transform the control frame of reference based on the tip frame of reference and/or the desired frame of reference.

Figure 23:
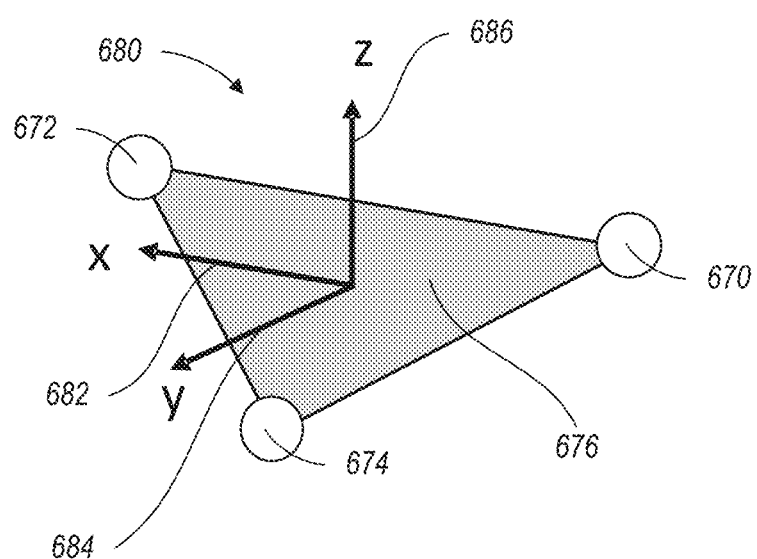
FIG. 23 describes a desired frame of reference determined by EM patch sensors, in accordance to an example embodiment.

FIG. 23 describes a desired frame of reference 680 that may be determined based on EM patch sensors, in accordance with one embodiment. FIG. 23 illustrates an approach for obtaining a desired frame of reference that may be determined from a world frame of reference. As shown in FIG. 23, one or more EM patch sensors (e.g., EM patch sensors 670, 672, and 674) may be placed on or near a patient (e.g., on a patient as shown by EM patch sensors 105 of FIG. 16, or on a bed on which the patient is lying). The EM patch sensors 670, 672, and 674 may form a plane 676 represented by a triangle whose vertices are at the locations of the EM patch sensors 670, 672, and 674. The desired frame of reference 680 may be determined based on the plane 676. In one embodiment, the x-axis 682 and the y-axis 684 may be parallel or in the plane 676, and the z-axis 686 may be perpendicular to the plane 676. In some aspects, the desired frame of reference 680 may be such that the negative z-axis of the frame of reference 680 (i.e., the direction opposite to the z-axis 686) may align or be at least roughly consistent with the direction of the gravitational force (e.g., when the patient is lying facing upward, and the EM patch sensors are placed on the body of the patient).

Adjusting the visual frame of reference and the control frame of reference using an anatomy-based approach will now be discussed. In accordance with one or more aspects of the present disclosure, FIGS. 24A-24D illustrate example user interfaces 780, 800, 820, and 840 that can be presented to a user during a process for correcting for uncommanded instrument roll (e.g., process 600 in FIG. 22) as described herein. For example, the user interfaces 780, 800, 820, or 840 can be presented on the display screen of the console 16 or 31 in some embodiments.

Figure 24A:
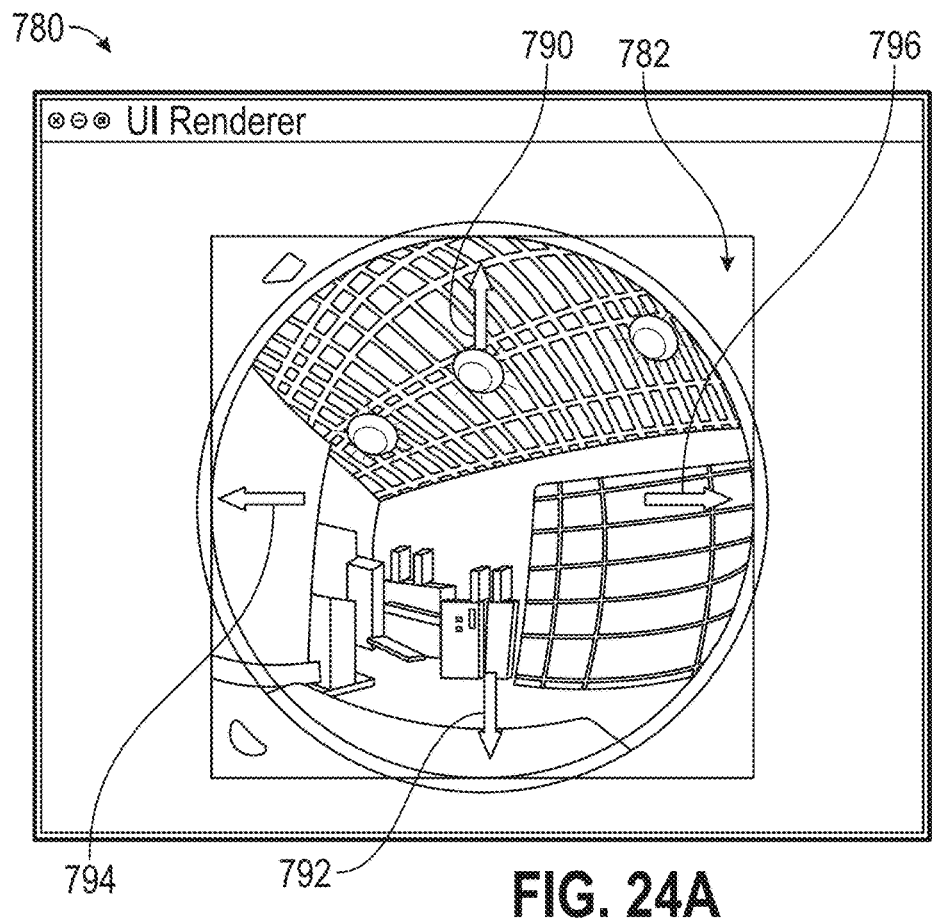
FIGS. 24A-24D describe exemplary user interfaces that can be presented to a user during a process for correcting for uncommanded instrument roll.

FIG. 24A illustrates an example user interface 780 that can be presented to a user before a medical instrument (e.g., medical instrument 350 or 450, medical instrument 70, or endoscope 13) is inserted into the patient. The example user interface 780 comprises a visual display 782, and one or more control frame indicators 790, 792, 794, and 796. The visual display 782 shows one or more images obtained from an imaging device (e.g., imaging device 315, 356, or 456) at or near the distal end of the medical instrument. As the medical instrument is not inserted into the patient, the visual display 782 shows an image of an outside world (e.g., an operating room). It is to be appreciated that the control frame indicators 790, 792, 794, and 796 are shown here to illustrate the mapping of user input-to-instrument control and may not be visually displayed in practice. However, embodiments that display visual indicators may display the indicators as any suitable shape (e.g., arrows, dots, or triangles). In some embodiments, there may be any number of control frame indicators on the example user interface 780. For example, there may be only one control frame indicator representing the up direction or the down direction. In another example, there may be two control frame indicators representing 1) one of the up direction and the down direction and 2) one of the left direction and the right direction. In yet another example, there may be more than four control frame indicators in addition to the up, down, left, and right directions.

In some embodiments, the visual frame of reference, the control frame of reference, and/or the tip frame of reference may be calibrated in air or before the instrument is inserted into the patient. For example, the directions and/or positions of the control frame indicators 790, 792, 794, and 796 (i.e., the control frame of reference) may be determined by the images from the imaging device (e.g., an image shown in the visual display 782), as described herein. As shown in FIG. 24A, in some examples, the control frame indicators 790, 792, 794, and 796 may be at least substantially consistent with the gravitational frame of reference. In addition, as shown in FIG. 24A, in some examples, the control frame indicators 790, 792, 794, and 796 may be at least substantially consistent with the visual frame of reference of the visual display 782. For example, the up, down, left, and right directions in the visual display 782 may at least substantially correspond to the up, down, left, and right directions of the control frame indicators 790, 792, 794, and 796.

Figure 24B:
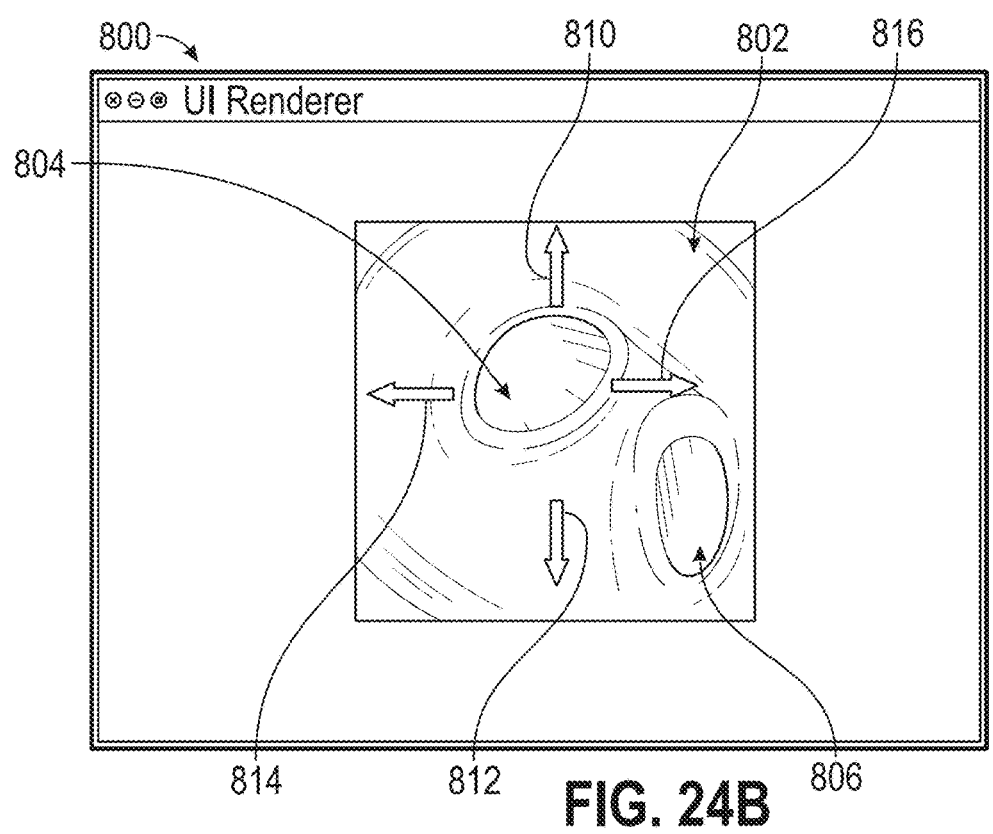

FIG. 24B illustrates an example user interface 800 that can be presented to a user when the medical instrument is inserted into the patient, and the distal end of the instrument has reached a certain area inside the patient (e.g., a main carina of the patient as shown in FIG. 24B). The example user interface 800 comprises a visual display 802 and one or more control frame indicators 810, 812, 814, and 816 representing a control frame of reference (e.g., the up, down, left, and right directions, respectively). In this example, because the medical instrument has reached the main carina of the patient, the visual display 802 shows an image of the main carina, with the left bronchus 804 and the right bronchus 806. The user interface 800 shown in FIG. 24B illustrates a display where uncommanded roll has occurred and no corrections to either the control frame of reference or the visual frame of reference has been made. This can be disorientating for the user of the system as one may expect the center lines of the airways to the left bronchus 804 and the right bronchus 806 to be substantially aligned. However, as shown in FIG. 24B, the right bronchus 806 is substantially rotated below the left bronchus 804. This rotation may cause the user of the system to adjust his knowledge of the anatomy to the rotated view presented by the medical instrument. Such an inconsistency may be due to uncommanded, unintended, and/or parasitic instrument roll artefacts as described above (e.g., an instrument roll due to an endotracheal insertion of the medical instrument).

Figure 24C:
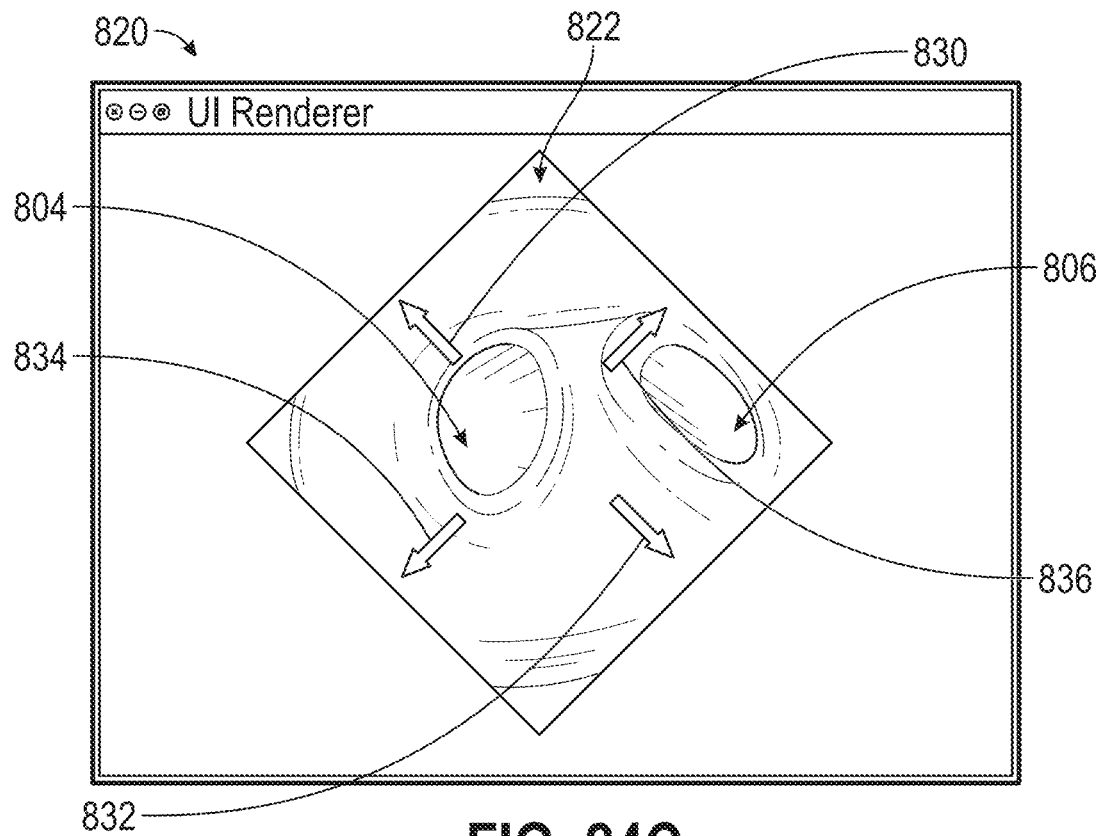

FIG. 24C illustrates an example user interface 820 that can be presented to a user after the visual frame of reference is transformed. The example user interface 820 comprises a visual display 822 and one or more control frame indicators 830, 832, 834, and 836 representing a control frame of reference (e.g., the up, down, left, and right directions, respectively). In contrast to the image of the visual display 802 in FIG. 24B, the visual frame of reference of the visual display 822 is transformed (e.g., rotated) such that the visual frame of reference is consistent with the anatomical frame of reference (e.g., the main carina). For example, the left bronchus 804 is located on the left side of the visual display 822, and the right bronchus 806 on the right side of the visual display 822. Methods to transform the visual frame of reference are described herein (e.g., based on a desired frame of reference, a tracked tip roll, the tip frame of reference, the gravitational frame of reference, and/or a frame of reference measured by one or more EM patch sensors such as, for example, EM patch sensors 105, 670, 672, and/or 674). In FIG. 24C, only the visual frame of reference is transformed to correspond to the anatomical frame of reference; the control frame of reference still remains inconsistent with the anatomical frame of reference. Such an inconsistency may provide control challenges to the operator of the medical instrument. For example, directing the medical instrument to actuate up will now cause the medical device to move diagonal up-right according to the view presented in the user interface 820.

Figure 24D:
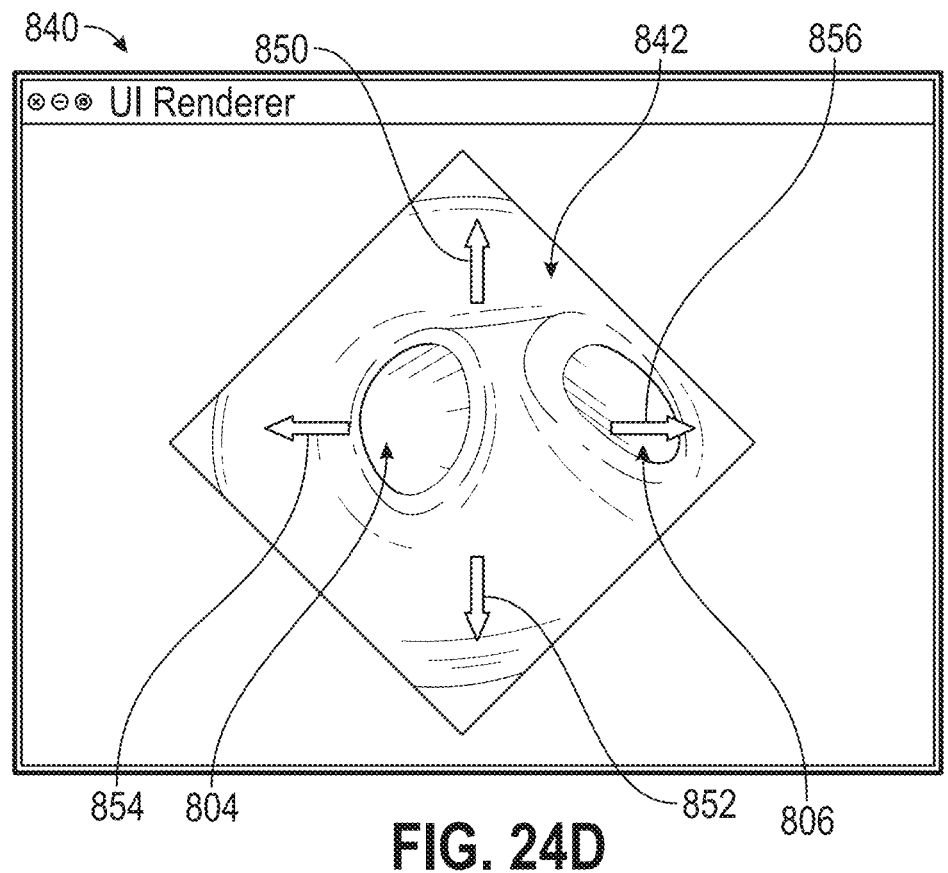

FIG. 24D illustrates an example user interface 840 that can be presented to a user after both the visual frame of reference and the control frame of reference are transformed. The example user interface 840 comprises a visual display 842 and one or more control frame indicators 850, 852, 854, and 856 representing a control frame of reference (e.g., the up, down, left, and right directions, respectively). In contrast to the visual display 822 in FIG. 24C, both the visual frame of reference and the control frame of reference shown in the visual display 842 are transformed (e.g., rotated) such that the visual frame of reference and the control frame of reference (as represented by the control frame indicators 850, 852, 854, and 856) are consistent with the anatomical frame of reference (e.g., the main carina). For example, the control frame indicator 854 representing the left direction corresponds to the location of the left bronchus 804, and the control frame indicator 856 representing the right direction corresponds to the location of the right bronchus 806. Methods to transform the control frame of reference are described herein (e.g., based on a desired frame of reference, a tracked tip roll, the tip frame of reference, the gravitational frame of reference, and/or a frame of reference measured by one or more EM patch sensors such as, for example, EM patch sensors 105, 670, 672, and/or 674).

Figure 25:
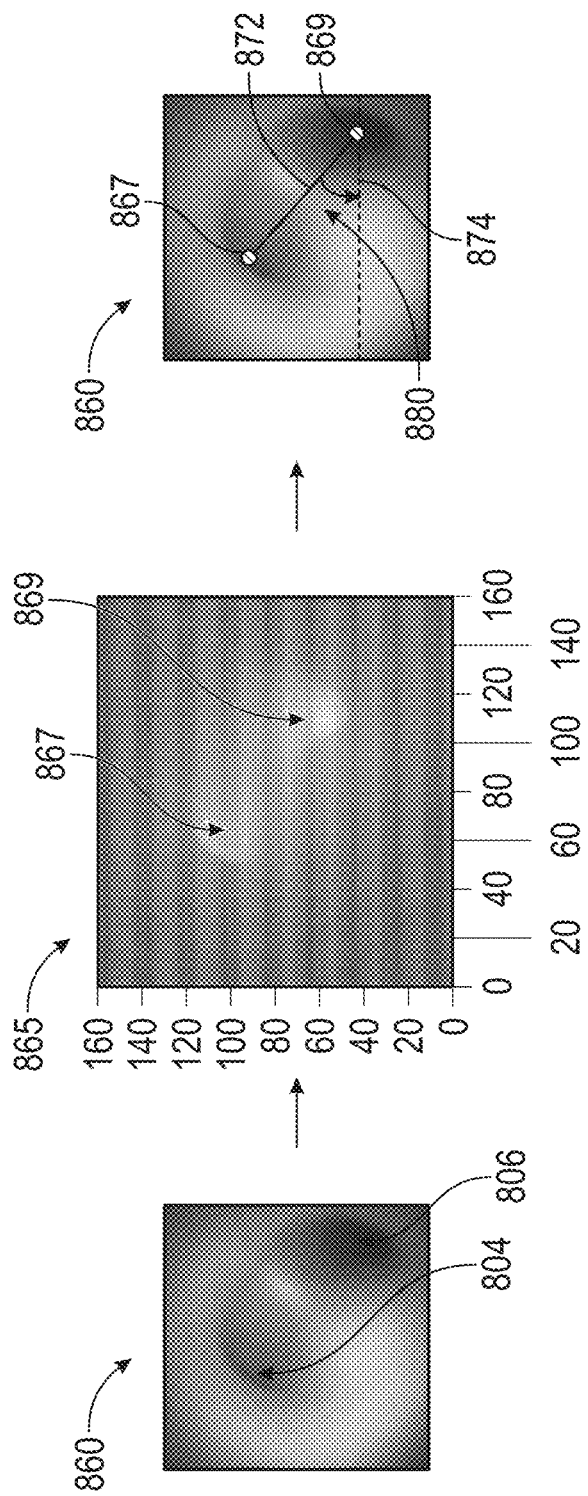
FIG. 25 depicts an exemplary process of determining an adjustment of an uncommanded instrument roll.

In accordance with one or more aspects of the present disclosure, FIG. 25 depicts an example process of determining an uncommanded roll. In some embodiments, the calculated uncommanded roll may be used to adjust the visual frame of reference and/or the control frame of reference. An image 860 derived from an imaging device (e.g., imaging device 315, 356, or 456) at or near the distal end of the medical instrument (e.g., medical instrument 350 or 450, medical instrument 70, or endoscope 13) shows the main carina of the patient, with the left bronchus 804 and the right bronchus 806. The image 860 shows that the visual frame of reference is not aligned with the anatomical frame of reference. In this example process, an anatomical characteristic (e.g., the main carina as shown in the image 860) is used as a landmark. Due to anatomical characteristics of lungs, a farthest depth point in the main carina is the right bronchus 806. The farthest depth point may be determined by various calculations such as, for example, a Shape From Shading (SFS) method.

The SFS method may first convert the image 860 derived from the imaging device to a shading image 865, in which each pixel of the shading image 865 represents a shading or brightness of the original image 860. In the shading image 865, the brightest pixel(s) are represented in darker colors, and the darkest pixel(s) are represented in lighter colors. The shading image 865 shows the locations of depth peaks 867 and 869 of the left bronchus 804 and the right bronchus 806, respectively. The system may be configured to locate the depth peaks 867 and 869 of the left bronchus 804 and the right bronchus 806, respectively, by, for example, searching for one or more local maximum pixels in the shading image 865.

The SFS method may then calculate a rotational adjustment of the visual frame of reference and/or the control frame of reference based on the locations of the depth peaks 267 and 869 of the left bronchus 804 and the right bronchus 806, respectively. The rotational adjustment 880 can be determined by calculating an angle between a horizontal line 874 of the original image 860 and a line 872 connecting the left bronchus 867 and the right bronchus 869. Thus, the rotational adjustment 880 to the visual frame of reference is made such that the line 872 connecting the two depth peaks 867 and 869 becomes horizontal; the left bronchus 804 locates on the left region of a transformed image; and right bronchus 806 locates on the right region of the transformed image. The rotational adjustment to the control frame of reference is calculated to be the same value with the rotational adjustment 880 to the visual frame of reference but in the opposite direction. The rotational adjustment to the control frame of reference makes the control frame of reference correspond to the anatomical frame of reference, as described above. In some embodiments, the process for determining an uncommanded roll or an adjustment to the visual frame of reference and/or the control frame of reference may be automated.

FIG. 26 describes a control system 900 configured to correct for an uncommanded instrument roll. The control system 910 can be implemented as one or more data storage devices and one or more hardware processors, for example, in a robotically controlled system (e.g., system 10, 36 or 47), an instrument driver (e.g., instrument driver 62), a controller (e.g. control circuitry 68), a console (e.g., console 16 or 31), and/or a console base (e.g., cart base 15), or component(s) thereof as described above.

The control system 900 comprises visual frame of reference data repository 902, control frame of reference data repository 904, tip frame of reference data repository 906, desired frame of reference data repository 908, processing module 910, transformed visual frame of reference data repository 912, and/or transformed control frame of reference data repository 914. Data of each of the input repositories 902, 904, 906, and 908 may be from a user input, one or more processors, or another data repository (e.g., gravitational frame of reference data repository). In some embodiments, the control system 900 may not have all of the input data repositories 902, 904, 906, and 908. In some embodiments, the control system 900 may comprise more than one of the input data repositories 902, 904, 906, and 908. In some embodiments, the control system 900 may not have all of the output data repositories 912 and 914. In some embodiments, the control system 900 may comprise more than one of the output data repositories 912 and 914. Though shown separately in FIG. 24 for purposes of clarity in the discussion below, it will be appreciated that some or all of the data repositories can be stored together in a single memory or set of memories.

The processing module 910 is configured to receive input data from the visual frame of reference data repository 902, the control frame of reference data repository 904, the tip frame of reference data repository 906, and/or the desired frame of reference data repository 908 and transmit output data to the transformed visual frame of reference data repository 912, and/or the transformed control frame of reference data repository 914. The processing module 910 comprises one or more processors and a non-transitory computer readable storage medium that stores instructions that, when executed, cause the processor(s) to conduct methods, processes, and steps described herein. For example, the instructions, when executed, may cause the processor(s) to at least: obtain a control frame of reference representing relationship between a motor control command and a motor output of a medical instrument configured to be inserted into a patient; determine a tip frame of reference based on data from at least one imaging device (e.g., imaging device 315, 356, or 456) or location sensor (e.g., EM coils 305 or 358, or EM patch sensors 105, 670, 672, or 674) at or near a distal end of the medical instrument, the tip frame of reference representing a current orientation of the distal end of the medical instrument; obtain a desired frame of reference based on data from the at least one imaging device or location sensor positioned on or near the patient; and determine one or more differences between (1) the control frame of reference and (2) the desired frame of reference. In one embodiment, the instructions, when executed, may cause the processor(s) to at least: transform the visual frame of reference and/or the control frame of reference based on the determined differences. In one embodiment, the instructions, when executed, may cause the processor(s) to at least: determine the one or more differences by comparing between data from the at least one imaging device or location sensor in the distal end of the medical instrument and data from one or more EM patches positioned on or near the patient.

Embodiments here have discussed approaches that determine a tip frame of reference via sensor data of the medical instrument and or other sensors externally located, such as patch sensors placed on the patient. Additionally or alternatively, other embodiments may estimate a tip frame of reference based on system setup or instrument shape. To illustrate, some embodiments may determine that a medical instrument will roll in a specified direction based on whether the instrument is being inserted into the patent from a given side. For example, if the medical device is inserted from the right side of the patient, the system may assume that the medical device will roll in a given direction. Similar determinations may be made based on a detected shape of the scope. Where the tip frame of reference is determined in this manner, the system may compare these estimated tip frame of references to the desired frame of reference or may be used to supplement the methods above to detect the tip frame of reference.

3. Implementing Systems and Terminology

Implementations disclosed herein provide systems, methods and apparatus for correcting for uncommanded instrument roll.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The correction, transformation and/or adjustment functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like.

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotically controlled steerable instrument system comprising:
   a steerable instrument comprising a proximal end, a distal end, and a channel extending therethrough, the steerable instrument configured to be inserted into a patient;
   one or more pullwires extending through and coupled to at least a portion of the steerable instrument;
   a robotic instrument driver;
   a control system communicatively coupled to the robotic instrument driver and configured to actuate the one or more pullwires;
   at least one computer-readable memory having stored thereon executable instructions; and
   one or more processors in communication with the at least one computer-readable memory and configured to execute the executable instructions to cause the robotically controlled steerable instrument system to at least:
      identify a control frame of reference representing a relationship between a motor control command and a motor output of the steerable instrument;
      determine a tip frame of reference based on data from at least one of an imaging device or location sensor at the distal end of the steerable instrument, the tip frame of reference representing a current orientation of the distal end of the steerable instrument;
      identify a desired frame of reference;
      determine a difference between the tip frame of reference and the desired frame of reference;
      determine an uncommanded roll of the steerable instrument based on the determination of the difference between the tip frame of reference and the desired frame of reference; and
      transform the control frame of reference based on the determination of the uncommanded roll of the steerable instrument.

2. The robotically controlled steerable instrument system of claim 1, wherein the location sensor comprises an electromagnetic (EM) sensor.

3. The robotically controlled steerable instrument system of claim 1, wherein the one or more processors in communication with the at least one computer-readable memory are configured to execute the executable instructions to cause the robotically controlled steerable instrument system to at least: (1) receive the data from the location sensor and (2) determine the tip frame of reference based on the data from the location sensor.

4. The robotically controlled steerable instrument system of claim 1, wherein the one or more processors in communication with the at least one computer-readable memory are configured to execute the executable instructions to cause the robotically controlled steerable instrument system to at least: receive data related to the control frame of reference from the control system.

5. The robotically controlled steerable instrument system of claim 1, wherein the one or more processors in communication with the at least one computer-readable memory are configured to execute the executable instructions to cause the robotically controlled steerable instrument system to at least: (1) actuate the one or more pullwires to move the portion of the steerable instrument and (2) determine the control frame of reference based on the movement of the portion of the steerable instrument.

6. The robotically controlled steerable instrument system of claim 1, wherein the one or more processors in communication with the at least one computer-readable memory are configured to execute the executable instructions to cause the robotically controlled steerable instrument system to at least: (1) receive the data from the imaging device, (2) determine a visual frame of reference based on the data from the imaging device, and (3) transform the visual frame of reference based on the tip frame of reference and the desired frame of reference.

7. The robotically controlled steerable instrument system of claim 1, wherein the one or more processors in communication with the at least one computer-readable memory are configured to execute the executable instructions to cause the robotically controlled steerable instrument system to at least: determine the desired frame of reference based on one or more anatomical features of the patient.

8. The robotically controlled steerable instrument system of claim 1, wherein the one or more processors in communication with the at least one computer-readable memory are configured to execute the executable instructions to cause the robotically controlled steerable instrument system to at least: (1) receive data from one or more sensors positioned on the patient, (2) determine a plane based on the data from the one or more sensors, (3) determine the desired frame of reference based on the plane.

9. The robotically controlled steerable instrument system of claim 1, wherein the one or more processors in communication with the at least one computer-readable memory are configured to execute the executable instructions to cause the robotically controlled steerable instrument system to at least:
   determine one or more differences between at least one image of an anatomical feature and at least one model of the anatomical feature; and
   transform the control frame of reference based on the one or more differences between the at least one image and the at least one model.

10. The robotically controlled steerable instrument system of claim 1, wherein the one or more processors in communication with the at least one computer-readable memory are configured to execute the executable instructions to cause the robotically controlled steerable instrument system to at least: rotate the control frame of reference with respect to a longitudinal axis of the steerable instrument to align with the desired frame of reference.

11. The robotically controlled steerable instrument system of claim 1, wherein the one or more processors in communication with the at least one computer-readable memory are configured to execute the executable instructions to cause the robotically controlled steerable instrument system to at least: transform the control frame of reference based on a user input.

12. The robotically controlled steerable instrument system of claim 1, wherein the one or more processors in communication with the at least one computer-readable memory are configured to further execute the executable instructions to cause the robotically controlled steerable instrument system to at least: verify the transformed control frame of reference.

13. The robotically controlled steerable instrument system of claim 1, wherein the one or more processors in communication with the at least one computer-readable memory are configured to further execute the executable instructions to cause the robotically controlled steerable instrument system to at least:
  actuate the one or more pullwires to move the portion of the steerable instrument;
  determine an expected change in the control frame of reference in response to the movement of the portion of the steerable instrument; and
  compare (1) an actual change in the control frame of reference and (2) the expected change.

14. The robotically controlled steerable instrument system of claim 1, wherein the steerable instrument further comprises a sheath configured to slidably cover at least a portion of the steerable instrument, and wherein the one or more processors in communication with the at least one computer-readable memory are configured to further execute the executable instructions to cause the robotically controlled steerable instrument system to at least:
  identify a sheath frame of reference representing an orientation of a distal end of the sheath; and
  transform the sheath frame of reference based on the control frame of reference or the desired frame of reference.

15. A non-transitory computer readable storage medium having stored thereon instructions that, when executed, cause at least one processor to at least:
  identify a control frame of reference representing a relationship between a motor control command and a motor output of a medical instrument configured to be inserted into a patient;
  determine a tip frame of reference based on data from at least one of an imaging device or location sensor at a distal end of the medical instrument, the tip frame of reference representing a current orientation of the distal end of the medical instrument;
  determine a desired frame of reference;
  determine one or more differences between the tip frame of reference and the desired frame of reference;
  determine that a current amount of roll of the medical instrument is out of alignment with an expected amount of roll for the medical instrument based on the determination of the one or more differences between the tip frame of reference and the desired frame of reference; and
  adjust the control frame of reference based on the determination that the current amount of roll of the medical instrument is out of alignment with the expected amount of roll for the medical instrument.

16. The non-transitory computer readable storage medium of claim 15, wherein the data is from the location sensor, the location sensor comprises an electromagnetic (EM) sensor.

17. The non-transitory computer readable storage medium of claim 15, wherein the instructions, when executed, cause the at least one processor to at least:
  determine the desired frame of reference based on at least one of a direction of gravity or a model of anatomy of the patient.

18. The non-transitory computer readable storage medium of claim 15, wherein the instructions, when executed, cause the at least one processor to at least:
  transform a visual frame of reference based on the determination that the current amount of roll of the medical instrument is out of alignment with the expected amount of roll for the medical instrument, the visual frame of reference representing an orientation of the imaging device at the distal end of the medical instrument.

19. A system comprising:
  one or more processors; and
  at least one computer-readable memory communicatively coupled to the one or more processors and storing executable instructions that, when executed by the one or more processors, cause the one or more processors to perform operations comprising:
    identifying a control frame of reference representing a relationship between a motor control command and a motor output of a medical instrument configured to be inserted into a patient;
    determining a tip frame of reference based on data from at least one of an imaging device or location sensor at a distal end of the medical instrument, the tip frame of reference representing a current orientation of the distal end of the medical instrument;
    determining an expected frame of reference;
    determining one or more differences between the tip frame of reference and the expected frame of reference;
    determining that a current amount of roll of the medical instrument is out of alignment with an expected amount of roll for the medical instrument based on the determination of the one or more differences between the tip frame of reference and the expected frame of reference; and
    adjusting the control frame of reference based on the determination that the current amount of roll of the medical instrument is out of alignment with the expected amount of roll for the medical instrument.

20. The system of claim 19, wherein the operations further comprise:
  based on robotic command data, causing a robotic component to control movement of the medical instrument, wherein the determining the expected frame of reference is based on the robotic command data.

* * * * *